US010675041B2

(12) United States Patent
Stokes et al.

(10) Patent No.: US 10,675,041 B2
(45) Date of Patent: Jun. 9, 2020

(54) REVERSE LOADING SURGICAL CLIP APPLIER

(71) Applicant: Ethicon LLC, Guaynabo, PR (US)

(72) Inventors: Michael J. Stokes, Cincinnati, OH (US); Chester Baxter, III, Loveland, OH (US); Tyler Brehm, Dayton, OH (US)

(73) Assignee: Ethicon LLC, Guaynabo, PR (US)

( * ) Notice: Subject to any disclaimer, the term of this patent is extended or adjusted under 35 U.S.C. 154(b) by 225 days.

(21) Appl. No.: 15/891,570

(22) Filed: Feb. 8, 2018

(65) Prior Publication Data

US 2019/0239888 A1    Aug. 8, 2019

(51) Int. Cl.
| | |
|---|---|
| *A61B 17/128* | (2006.01) |
| *A61B 17/122* | (2006.01) |
| *A61B 34/00* | (2016.01) |
| *A61B 34/37* | (2016.01) |
| *A61B 17/10* | (2006.01) |

(Continued)

(52) U.S. Cl.
CPC ........ *A61B 17/1285* (2013.01); *A61B 17/122* (2013.01); *A61B 34/25* (2016.02); *A61B 34/37* (2016.02); *A61B 17/10* (2013.01); *A61B 17/2909* (2013.01); *A61B 34/70* (2016.02); *A61B 2017/00017* (2013.01); *A61B 2017/00371* (2013.01); *A61B 2017/00398* (2013.01); *A61B 2017/00477* (2013.01);

(Continued)

(58) Field of Classification Search
CPC ..... A61B 17/1285; A61B 34/37; A61B 34/25; A61B 17/122; A61B 2017/00371; A61B 2017/00398; A61B 2017/00017; A61B 2017/2927; A61B 17/2909; A61B 2017/2939; A61B 34/70; A61B 2034/305; A61B 2017/00477; A61B 17/10

See application file for complete search history.

(56) References Cited

U.S. PATENT DOCUMENTS

| | | | |
|---|---|---|---|
| 5,409,498 A * | 4/1995 | Braddock | .......... A61B 17/1285 227/901 |
| 5,484,095 A | 1/1996 | Green et al. | |

(Continued)

FOREIGN PATENT DOCUMENTS

AU    2014277777 A1    1/2015

OTHER PUBLICATIONS

ISRWO from PCT/IB2019/050351 (claiming priority to the present application) dated May 2, 2019.

*Primary Examiner* — Julian W Woo

(74) *Attorney, Agent, or Firm* — Vorys, Sater, Seymour and Pease LLP

(57) ABSTRACT

An end effector for a surgical clip applier includes a body having a proximal end and a distal end, a clip cartridge coupled to the body and containing one or more surgical clips, and a head rotatably coupled to the distal end. First and second jaw members are mounted to the head such that rotation of the head correspondingly moves the first and second jaw members. The head is rotatable between a loading position, where the first and second jaw members are aligned to receive a distal-most surgical clip of the one or more surgical clips, and a clamping position, where the first and second jaw members are positioned to crimp a surgical clip interposing the first and second jaw members.

18 Claims, 12 Drawing Sheets

(51) Int. Cl.
  *A61B 17/00*  (2006.01)
  *A61B 34/30*  (2016.01)
  *A61B 17/29*  (2006.01)
(52) U.S. Cl.
  CPC .............. *A61B 2017/2927* (2013.01); *A61B 2017/2939* (2013.01); *A61B 2034/305* (2016.02)

(56) References Cited

U.S. PATENT DOCUMENTS

| | | | |
|---|---|---|---|
| 5,634,584 A * | 6/1997 | Okorocha | A61B 17/0682 227/176.1 |
| 8,403,945 B2 | 3/2013 | Whitfield et al. | |
| 8,968,337 B2 * | 3/2015 | Whitfield | A61B 17/1285 606/143 |
| 9,232,979 B2 | 1/2016 | Parihar et al. | |
| 2011/0224696 A1 | 9/2011 | Huitema et al. | |
| 2016/0249933 A1 | 9/2016 | Whitfield et al. | |
| 2016/0287252 A1 | 10/2016 | Parihar | |

* cited by examiner

REVERSE LOADING SURGICAL CLIP APPLIER

BACKGROUND

Minimally invasive surgical (MIS) tools and procedures are often preferred over traditional open surgical approaches due to their propensity toward reducing post-operative recovery time and leaving minimal scarring. Endoscopic surgery is one type of MIS procedure in which a surgical tool operably connected to an elongate shaft is introduced into the body of a patient through a natural bodily orifice. Laparoscopic surgery is a related type of MIS procedure in which a small incision is formed in the abdomen of a patient and a trocar is inserted through the incision to form a surgical access pathway for a surgical tool and elongate shaft. Once located within the abdomen, the surgical tool engages and/or treats tissue in a number of ways to achieve a diagnostic or therapeutic effect. Manipulation and engagement of the surgical tool may take place via various components passing through the elongate shaft.

One surgical instrument commonly used with a trocar is a surgical clip applier, which can be used to ligate blood vessels, ducts, shunts, or portions of body tissue during surgery. Traditional surgical clip appliers have a handle and an elongate shaft extending from the handle. A pair of movable opposed jaws is positioned at the end of the elongate shaft for holding and forming a surgical clip or "ligation clip" therebetween. In operation, a user (e.g., a surgeon or clinician) positions the jaws around the vessel or duct and squeezes a trigger on the handle to close the jaws and thereby collapse the surgical clip over the vessel.

More recently, however, robotic systems have been developed to assist in MIS procedures. Instead of directly engaging a surgical instrument, users are now able to manipulate and engage surgical instruments via an electronic interface communicatively coupled to a robotic manipulator. With the advances of robotic surgery, a user need not even be in the operating room with the patient during the surgery.

Robotic surgical systems are also now capable of utilizing robotically controlled clip appliers. Such clip appliers include features for robotically feeding and forming surgical clips. Advances and improvements to the methods and devices for applying surgical clips to vessels, ducts, shunts, etc. is continuously in demand to make the process more efficient and safe.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to surgical systems and, more particularly, to surgical clip appliers with jaws that are rotatable to feed surgical clips between opposed jaw members.

Embodiments discussed herein describe improvements to clip applier end effectors. The end effectors described herein include a body having a proximal end and a distal end, a clip cartridge coupled to the body and containing one or more surgical clips, and a head rotatably coupled to the distal end. First and second jaw members are mounted to the head such that rotation of the head correspondingly moves the first and second jaw members. The head may be rotatable between a loading position, where the first and second jaw members are aligned to receive a distal-most surgical clip of the one or more surgical clips, and a clamping position, where the first and second jaw members are positioned to crimp a surgical clip interposing the first and second jaw members.

In contrast to conventional clip appliers, the surgical clips may be received by the jaw members crown first, which helps mitigate catching the surgical clips on any sharp corners that might obstruct their distal advancement. Moreover, the presently described jaw members may comprise independent or separate plate-like structures that may prove advantageous in facilitating parallel closure of the jaw members, which can reduce the force required to crimp a surgical clip.

Figure 1:
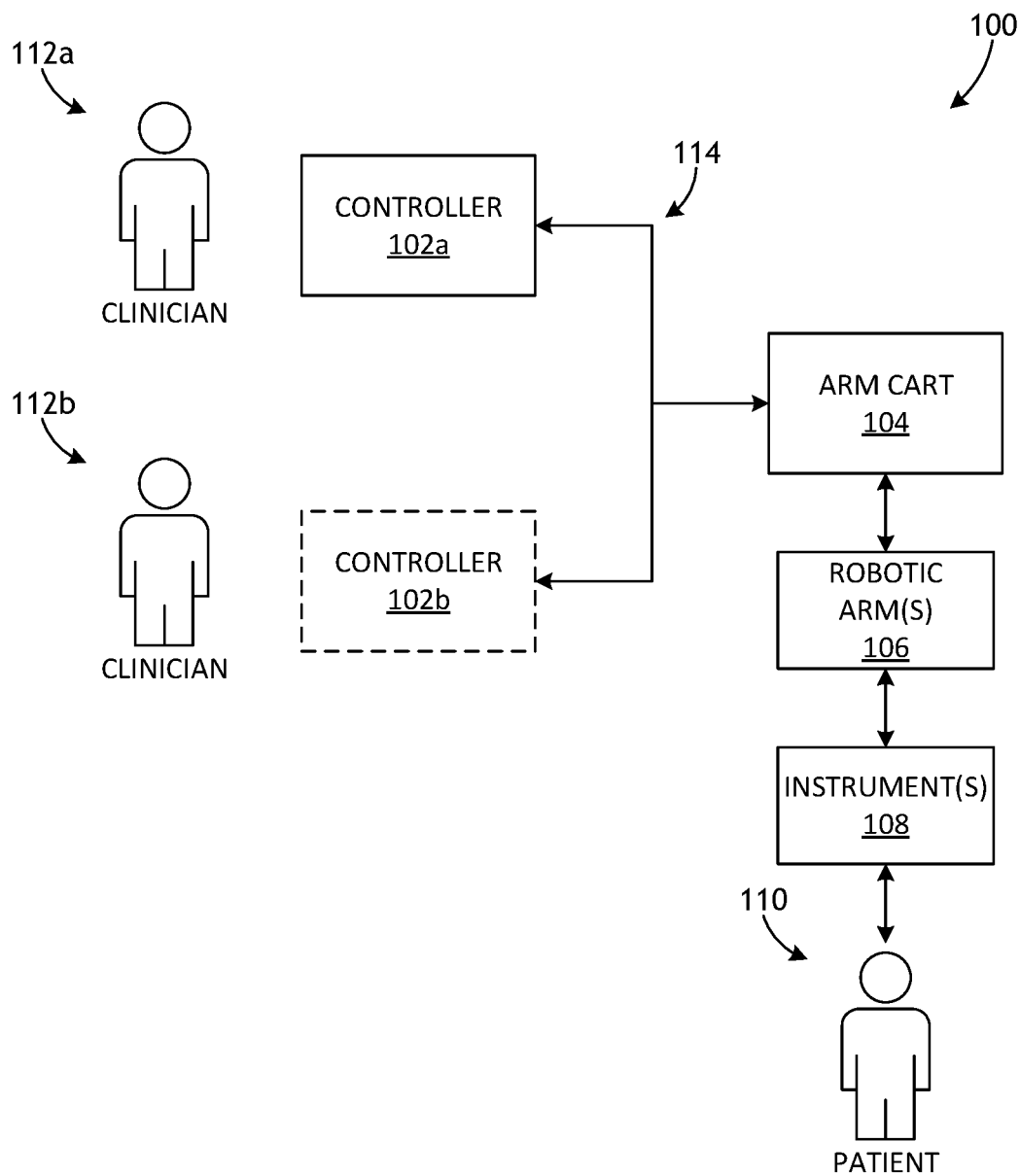
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112a (e.g., a surgeon) from the master controller 102a.

In some embodiments, a second master controller 102b (shown in dashed lines) operated by a second clinician 112b may also direct operation of the robotic arms 106 and instruments 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional arm carts (not shown) having additional robotic arms (not shown) may be utilized during surgery on a patient 110, and these additional robotic arms may be controlled by one or more of the master controllers 102a,b.

The arm cart 104 and the master controllers 102a,b may be in communication with one another via a communications link 114, which may be any type of wired or wireless telecommunications means configured to carry a variety of communication signals (e.g., electrical, optical, infrared, etc.) according to any communications protocol.

The master controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical instrument(s) 108, for example, for opening and closing opposing jaws, applying an electrical potential (current) to an electrode, or the like. The master controllers 102a,b can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand the various embodiments and forms of the various embodiments of robotic surgery apparatus, systems, and methods disclosed herein.

Figure 2:
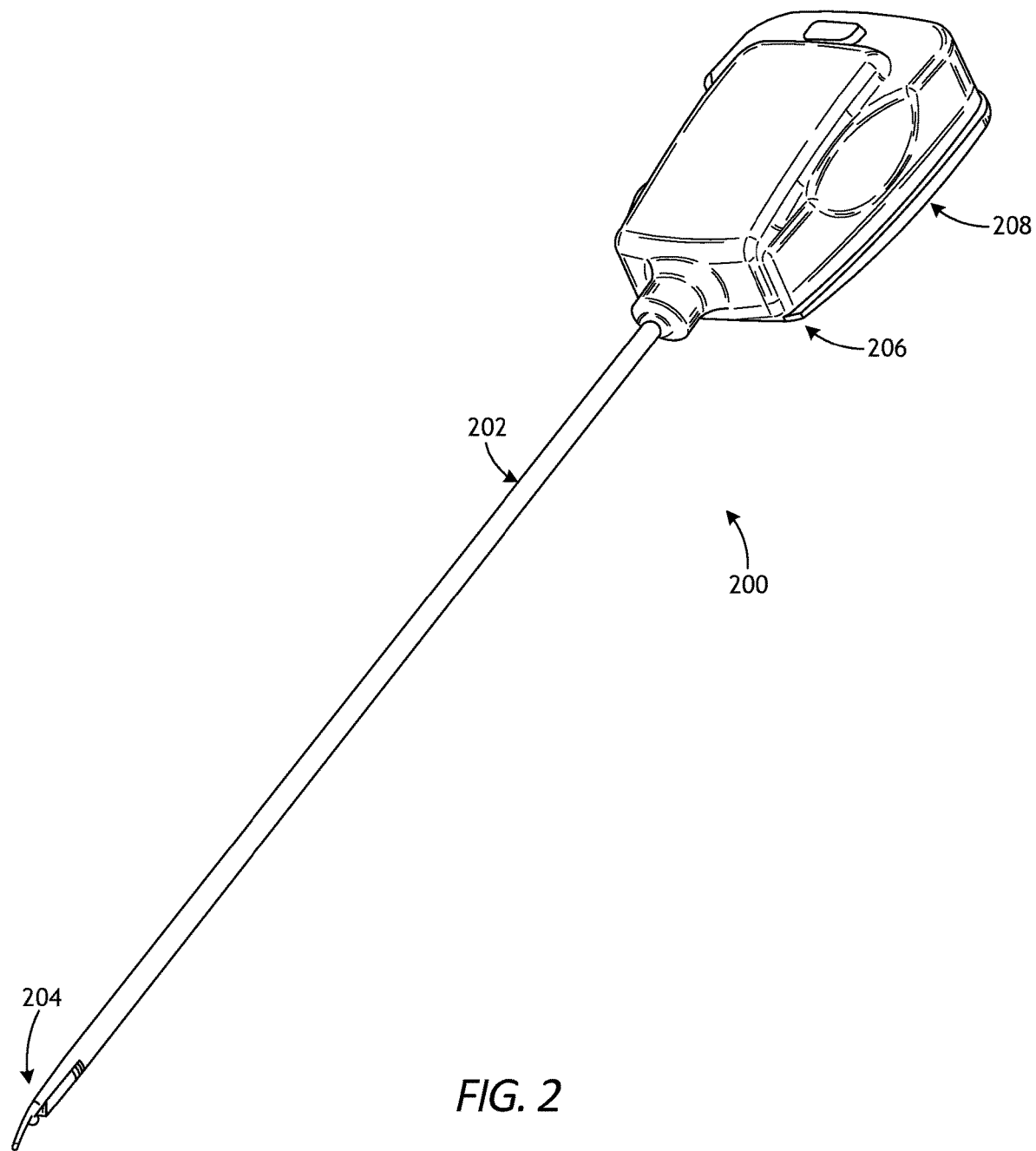
FIG. 2 is an isometric top view of an example surgical tool that may incorporate some or all of the principles of the present disclosure.

FIG. 2 is an isometric top view of an example surgical tool 200 that may incorporate some or all of the principles of the present disclosure. The surgical tool 200 may be the same as or similar to the surgical instrument(s) 108 of FIG. 1 and, therefore, may be used in conjunction with the robotic surgical system 100 of FIG. 1. Accordingly, the surgical tool 200 may be designed to be releasably coupled to a robotic arm 106 (FIG. 1) of a robotic manipulator of the robotic surgical system 100. Full detail and operational description of the surgical tool 200 is provided in U.S. Patent Pub. 2016/0287252, entitled "Clip Applier Adapted for Use with a Surgical Robot," the contents of which are hereby incorporated by reference in their entirety.

While the surgical tool 200 is described herein with reference to a robotic surgical system, it is noted that the principles of the present disclosure are equally applicable to non-robotic surgical tools or, more specifically, manually operated surgical tools. Accordingly, the discussion provided herein relating to robotic surgical systems merely encompasses one example application of the presently disclosed inventive concepts.

As illustrated, the surgical tool 200 can include an elongate shaft 202, an end effector 204 coupled to the distal end of the shaft 202, and a drive housing 206 coupled to the proximal end of the shaft 202. The terms "proximal" and "distal" are defined herein relative to a robotic surgical system having an interface configured to mechanically and electrically couple the surgical tool 200 (e.g., the drive housing 206) to a robotic manipulator. The term "proximal" refers to the position of an element closer to the robotic manipulator and the term "distal" refers to the position of an element closer to the end effector 204 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

In applications where the surgical tool 200 is used in conjunction with a robotic surgical system (e.g., system 100 of FIG. 1), the drive housing 206 can include a tool mounting portion 208 designed with features that releasably couple the surgical tool 200 to a robotic arm (e.g., the robotic arms 106 or "tool drivers" of FIG. 1) of a robotic manipulator. The tool mounting portion 208 may releasably attach (couple) the drive housing 206 to a tool driver in a variety of ways, such as by clamping thereto, clipping thereto, or slidably mating therewith. In some embodiments, the tool mounting portion 208 may include an array of electrical connecting pins, which may be coupled to an electrical connection on the mounting surface of the tool driver. While the tool mounting portion 208 is described herein with reference to mechanical, electrical, and magnetic coupling elements, it should be understood that a wide variety of telemetry modalities might be used, including infrared, inductive coupling, or the like.

Figure 3:
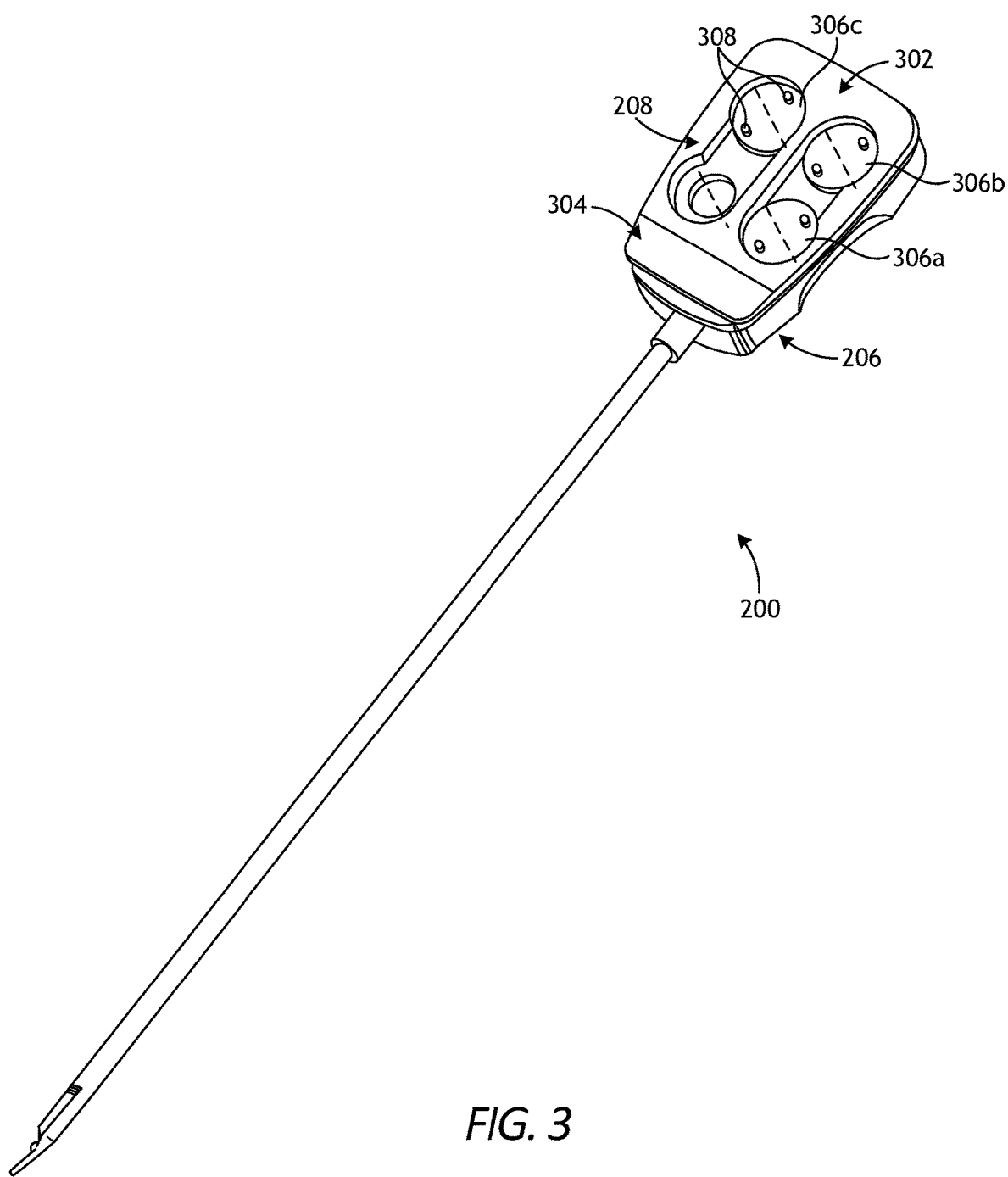
FIG. 3 is an isometric bottom view of the surgical tool of FIG. 2.

FIG. 3 is an isometric bottom view of the surgical tool 200. The surgical tool 200 further includes an interface 302 that mechanically and electrically couples the tool mounting portion 208 to a robotic manipulator. In various embodiments, the tool mounting portion 208 includes a tool mounting plate 304 that operably supports a plurality of drive inputs, shown as a first drive input 306a, a second drive input 306b, and a third drive input 306c. While only three drive inputs 306a-c are shown in FIG. 3, more or less than three may be employed, without departing from the scope of the disclosure.

In the illustrated embodiment, each drive input 306a-c comprises a rotatable disc configured to align with and couple to a corresponding input actuator (not shown) of a given tool driver. Moreover, each drive input 306a-c provides or defines one or more surface features 308 configured to align with mating surface features provided on the corresponding input actuator. The surface features 308 can include, for example, various protrusions and/or indentations that facilitate a mating engagement.

Figure 4:
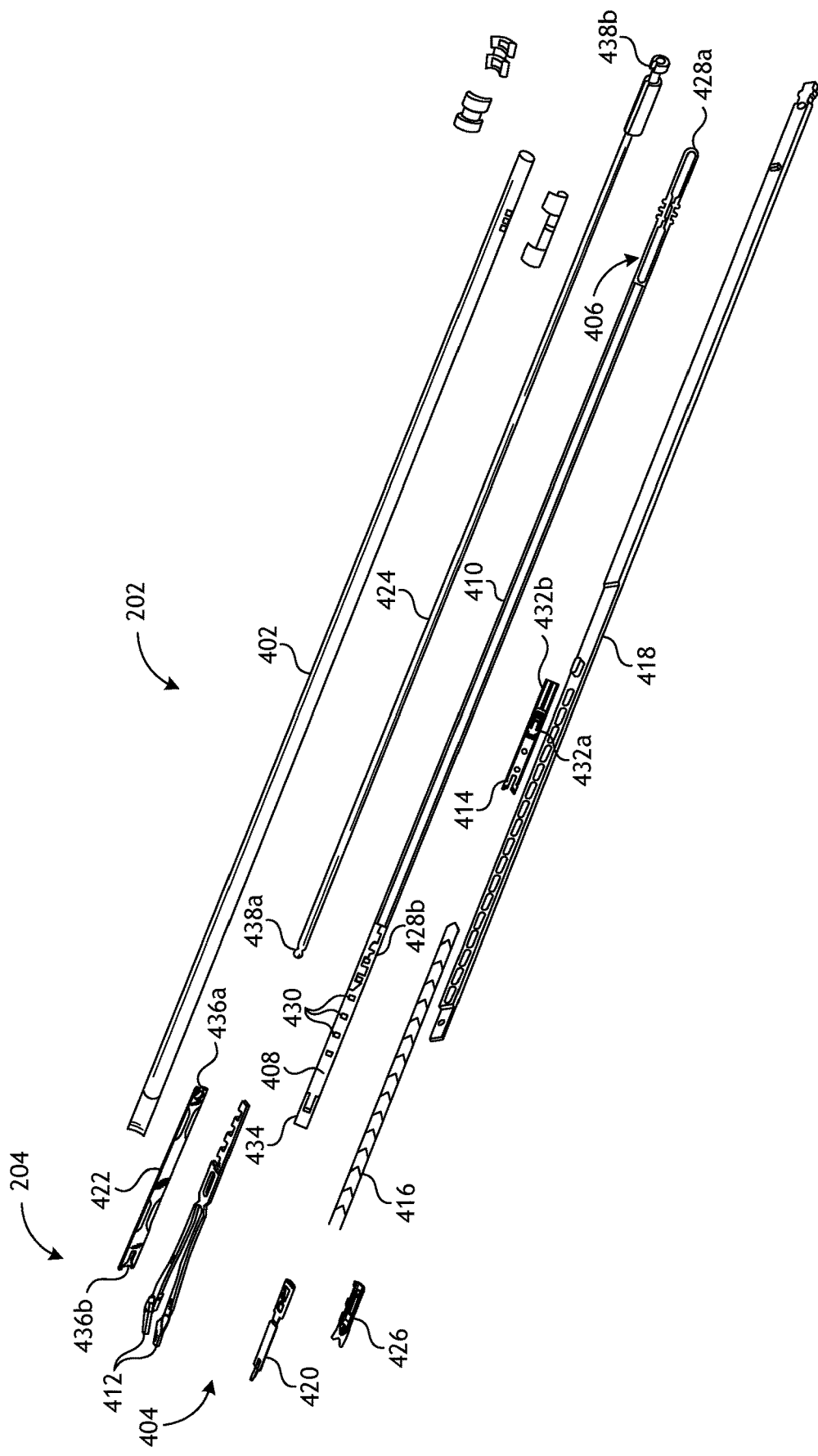
FIG. 4 is an exploded view of the elongate shaft and the end effector of the surgical tool of FIGS. 2 and 3.

FIG. 4 is an exploded view of one example of the elongate shaft 202 and the end effector 204 of the surgical tool 200 of FIGS. 2 and 3, according to one or more embodiments. As illustrated, the shaft 202 includes an outer tube 402 that houses the various components of the shaft 202, which can include a jaw retaining assembly 404. The jaw retaining assembly 404 includes a jaw retainer shaft 406 with a clip track 408 and a push rod channel 410 formed thereon. The end effector 204 includes opposing jaws 412 that are configured to mate to a distal end of the clip track 408.

The shaft 202 also includes a clip advancing assembly, which, in one example embodiment, can include a feeder shoe 414 adapted to be slidably disposed within the clip track 408. The feeder shoe 414 is designed to advance a series of clips 416 positioned within the clip track 408, and a feedbar 418 is adapted to drive the feeder shoe 414 through the clip track 408. An advancer assembly 420 is adapted to mate to a distal end of the feedbar 418 for advancing a distal-most clip into the jaws 412.

The shaft 202 furthers include a clip forming or camming assembly operable to collapse the jaws 412 and thereby crimp (crush) a surgical clip 416 positioned between (interposing) the jaws 412. The camming assembly includes a cam 422 that slidably mates to the jaws 412, and a push rod 424 that moves the cam 422 relative to the jaws 412 to collapse the jaws 412. A tissue stop 426 can mate to a distal end of the clip track 408 to help position the jaws 412 relative to a surgical site.

The jaw retainer shaft 406 is extendable within and couples to the outer tube 402 at a proximal end 428a, and its distal end 428b is adapted to mate with the jaws 412. The push rod channel 410 formed on the jaw retainer shaft 406 may be configured to slidably receive the push rod 424, which is used to advance the cam 422 over the jaws 412. The clip track 408 extends distally beyond the distal end 428b of the jaw retainer shaft 406 to allow a distal end of the clip track 408 to be substantially aligned with the jaws 412.

The clip track 408 can include several openings 430 formed therein for receiving an upper or "superior" tang 432a formed on the feeder shoe 414 adapted to be disposed within the clip track 408. The clip track 408 can also include a stop tang 434 formed thereon that is effective to be engaged by a corresponding stop tang formed on the feeder shoe 414 to prevent movement of the feeder shoe 414 beyond a distal-most position. To facilitate proximal movement of the feeder shoe 414 within the clip track 408, the feeder shoe 414 can also include a lower or "inferior" tang 432b formed on the underside thereof for allowing the feeder shoe 414 to be engaged by the feedbar 418 as the feedbar 418 is moved distally. In use, each time the feedbar 418 is moved distally, a detent formed in the feedbar 418 engages the inferior tang 432b and moves the feeder shoe 414 distally a predetermined distance within the clip track 408. The feedbar 418 can then be moved proximally to return to its initial position, and the angle of the inferior tang 432b allows the inferior tang 432b to slide into the next detent formed in the feedbar 418.

The jaws 412 include first and second opposed jaw members that are movable (collapsible) relative to one another and are configured to receive a surgical clip from the series of clips 416 therebetween. The jaw members can each include a groove formed on opposed inner surfaces thereof for receiving the legs of a surgical clip 416 in alignment with the jaw members. In the illustrated embodiment, the jaw members are biased to an open position and a force is required to urge the jaw members toward one another to crimp the interposing clip 416. The jaw members can also each include a cam track formed thereon for allowing the cam 422 to slidably engage and move the jaw members toward one another. A proximal end 436a of the cam 422 is matable with a distal end 438a of the push rod 424, and a distal end 436b of the cam 422 is adapted to engage and actuate the jaws 412. The proximal end 438b of the push rod 424 is matable with a closure link assembly associated with the drive housing 206 for moving the push rod 424 and the cam 422 relative to the jaws 412.

The distal end 436b of the cam 422 includes a camming channel or tapering recess formed therein for slidably receiving corresponding cam tracks provided by the jaw members. In operation, the cam 422 is advanced from a proximal position, in which the jaw members are spaced apart from one another, to a distal position, where the jaw members are collapsed to a closed position. As the cam 422 is advanced over the jaw members, the tapering recess at the distal end 436b serves to push the jaw members toward one another, thereby crimping a surgical clip 416 disposed therebetween.

Figure 5:
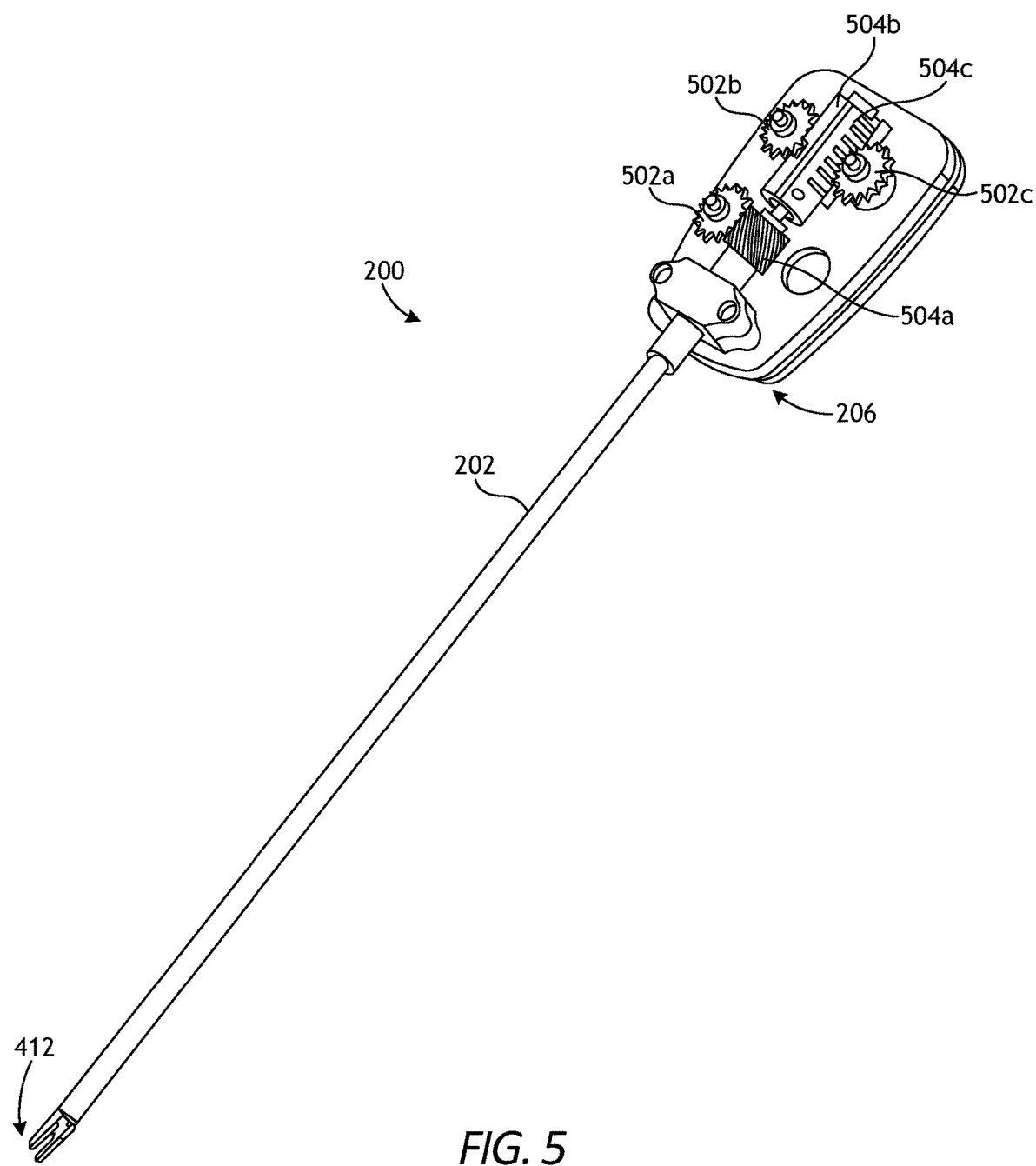
FIG. 5 is an exposed isometric view of the surgical tool of FIG. 2.

FIG. 5 is an exposed isometric view of the surgical tool 200 of FIG. 2, according to one or more embodiments. The shroud or covering of the drive housing 206 has been removed to reveal the internal component parts. As illustrated, the surgical tool 200 may include a first drive gear 502a, a second drive gear 502b, and a third drive gear 502c. The first drive gear 502a may be operatively coupled to (or extend from) the first drive input 306a (FIG. 3) such that actuation of the first drive input 306a correspondingly rotates the first drive gear 502a. Similarly, the second and third drive gears 502b,c may be operatively coupled to (or extend from) the second and third drive inputs 306b,c (FIG. 3), respectively, such that actuation of the second and third drive inputs 306b,c correspondingly rotates the second and third drive gears 502b,c, respectively.

The first drive gear 502a may be configured to intermesh with a first driven gear 504a, which is operatively coupled to the shaft 202. In the illustrated embodiment, the driven gear 504a comprises a helical gear. In operation, rotation of the first drive gear 502a about a first axis correspondingly rotates the first driven gear 504a about a second axis orthogonal to the first axis to control rotation of the shaft 202 in clockwise and counter-clockwise directions based on the rotational direction of the first drive gear 502a.

The second drive gear 502b may be configured to intermesh with a second driven gear 504b (partially visible in FIG. 5), and the third drive gear 502c may be configured to intermesh with a third driven gear 504c. In the illustrated embodiment, the second and third drive and driven gears 502b,c, 504b,c comprise corresponding rack and pinion interfaces, where the driven gears 504b,c comprise the rack and the drive gears 502b,c comprise the pinion. Independent rotation of the second and third drive gears 502b,c will cause the second and third driven gears 504b,c, respectively, to translate linearly relative to (independent of) one another.

In at least one embodiment, actuation (rotation) of the third drive gear 502c will result in a surgical clip 416 (FIG. 4) being fed into the jaws 412. More particularly, the third driven gear 504c may be operatively coupled to the feedbar 418 (FIG. 4) and, upon rotation of the third drive gear 502c in a first angular direction, the third driven gear 504c will advance distally and correspondingly advance the feedbar 418 a sufficient distance to fully advance a surgical clip into the jaws 412. Rotation of the third drive gear 502c may be precisely controlled by an electrical and software interface to deliver the exact linear travel to the third driven gear 504c necessary to feed a clip 416 into the jaws 412.

Upon delivery of a clip into the jaws 412, or after a predetermined amount of rotation of the third drive gear 502c, rotation of the third drive gear 502c is reversed in a second angular direction to move the third driven gear 504c linearly in a proximal direction, which correspondingly moves the feedbar 418 proximally. This process may be repeated several times to accommodate a predetermined number of clips residing in the shaft 202.

Actuation of the second drive gear 502b causes the jaws 412 to close or collapse to crimp a surgical clip. More particularly, the second driven gear 504b may be coupled to the proximal end 438b (FIG. 4) of the push rod 424 (FIG. 4) and, upon actuation of the second drive gear 502b in a first angular direction, the second driven gear 504b will be advanced linearly in a distal direction and correspondingly drive the push rod 424 distally, which drives the cam 422 over the jaws 412 to collapse the jaw members and crimp a surgical clip positioned in the jaws 412. Once a surgical clip is successfully deployed, rotation of the second drive gear 502b is reversed in the opposite angular direction to move the second driven gear 504b in a proximal direction, which correspondingly moves the push rod 424 and the cam 422 proximally and permits the jaws 412 to open once again.

The processes of delivering a surgical clip into the jaws 412 and collapsing the jaws 412 to crimp the surgical clip are not limited to the actuation mechanisms and structures described herein. In alternative embodiments, for example, the second and third driven gears 504b,c may instead comprise capstan pulleys configured to route and translate drive cables within the shaft 202. In such embodiments, the drive cables may be operatively coupled to one or more lead screws or other types of rotating members positioned within the shaft 202 near the distal end and capable of advancing the feedbar 418 to deliver a surgical clip into the jaws 412 and advancing the cam 422 to collapse the jaws 412 and crimp the surgical clip.

Figure 6:
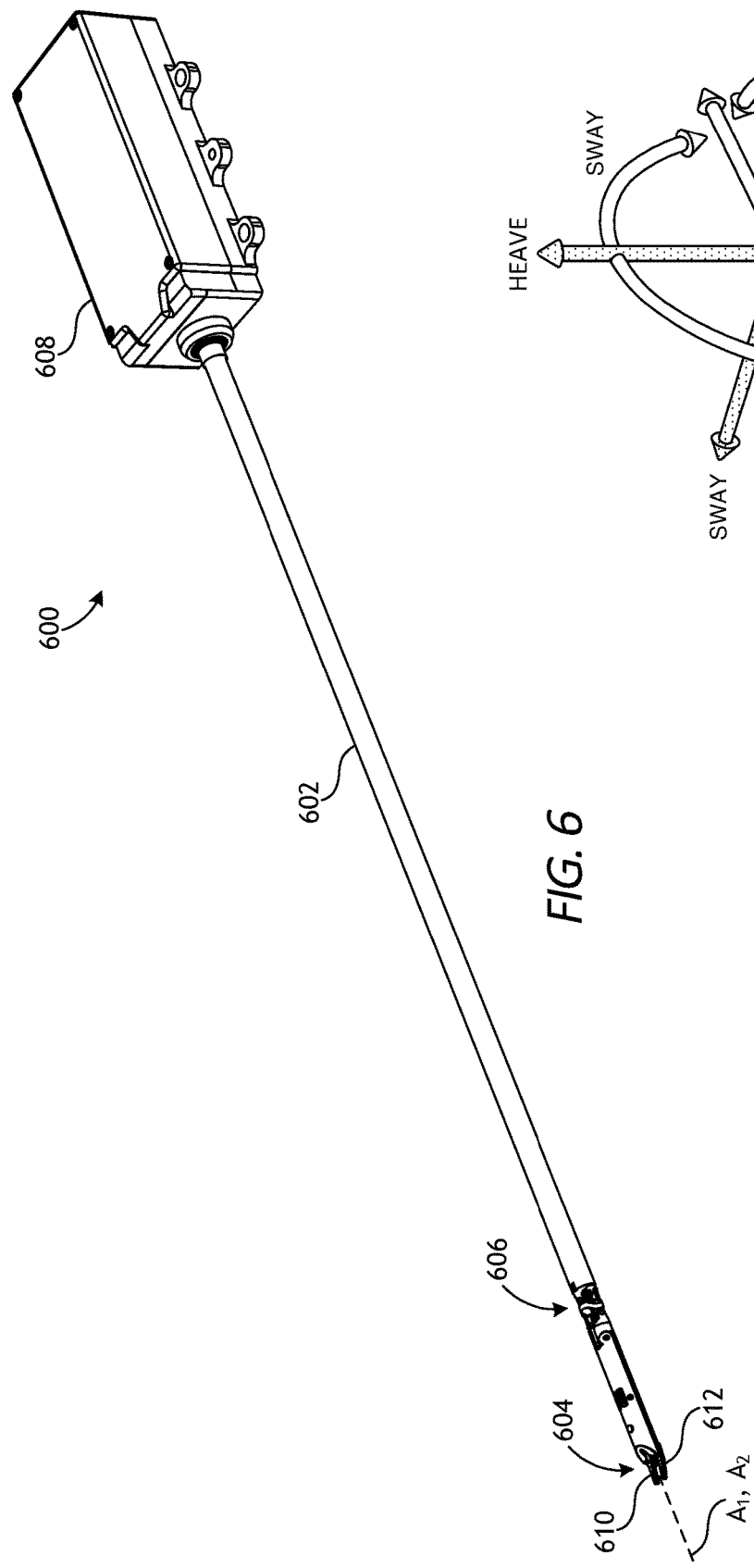
FIG. 6 is a side view of an example surgical tool that may incorporate some or all of the principles of the present disclosure.

FIG. 6 is an isometric top view of another example surgical tool 600 that may incorporate some or all of the principles of the present disclosure. Similar to the surgical tool 200 of FIG. 2, the surgical tool 600 may be used in conjunction with the robotic surgical system 100 of FIG. 1. As illustrated, the surgical tool 600 includes an elongate shaft 602, an end effector 604 positioned at the distal end of the shaft 602, a wrist 606 (alternately referred to as a "articulable wrist joint") that couples the end effector 604 to the distal end of the shaft 602, and a drive housing 608 coupled to the proximal end of the shaft 602. In some embodiments, the shaft 602, and hence the end effector 604 coupled thereto, is configured to rotate about a longitudinal axis $A_1$.

In the illustrated embodiment, the end effector 604 comprises a clip applier that includes opposing jaw members 610, 612 configured to collapse toward one another to crimp a surgical clip. The wrist 606 comprises an articulatable joint that facilitates pivoting movement of the end effector 604 relative to the shaft 602 to position the end effector 604 at desired orientations and locations relative to a surgical site. The housing 608 includes (contains) various actuation mechanisms designed to control articulation and operation of the end effector 604.

Figure 7:
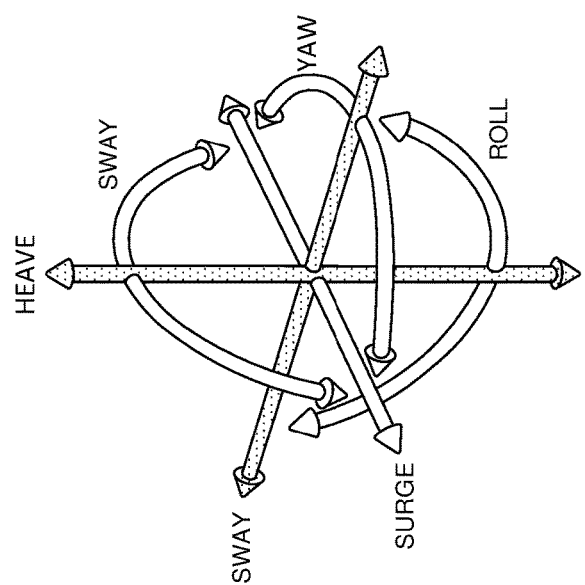
FIG. 7 illustrates potential degrees of freedom in which the wrist of FIG. 1 may be able to articulate (pivot).

FIG. 7 illustrates the potential degrees of freedom in which the wrist 606 may be able to articulate (pivot). The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane.

Referring again to FIG. 6, the surgical tool 600 includes a plurality of drive cables (generally obscured in FIG. 6) that form part of a cable driven motion system configured to facilitate operation and articulation (movement) of the end effector 604 relative to the shaft 602. For example, selectively moving the drive cables can actuate the end effector 604 and thereby collapse the jaw members 610, 612 toward each other. Moreover, moving the drive cables can also move the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. In the articulated position, the longitudinal axes $A_1$, $A_2$ would be angularly offset from each other such that the end effector 604 is at a non-zero angle relative to the shaft 602.

Figure 8:
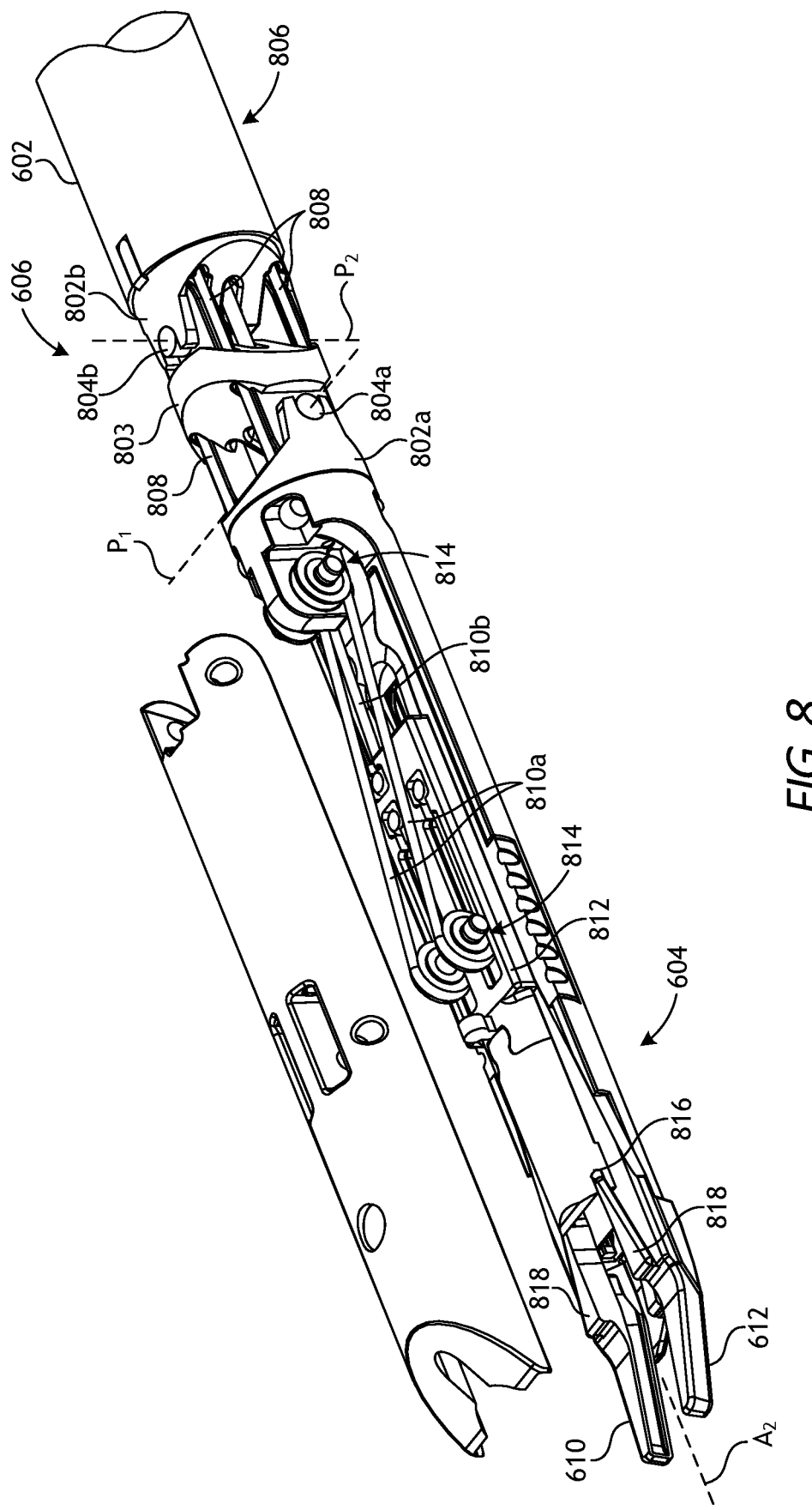
FIG. 8 is an enlarged isometric view of the distal end of the surgical tool of FIG. 6.

FIG. 8 is an enlarged isometric view of the distal end of the surgical tool 600 of FIG. 6. More specifically, FIG. 8 depicts an enlarged and partially exploded view of the end effector 604 and the wrist 606. The wrist 606 operatively couples the end effector 604 to the shaft 602. To accomplish this, the wrist 606 includes a distal clevis 802a, a proximal clevis 802b, and a spacer 803 interposing the distal and proximal clevises 802a,b. The end effector 604 is coupled to the distal clevis 802a and the distal clevis 802a is rotatably mounted to the spacer 803 at a first axle 804a. The spacer 803 is rotatably mounted to the proximal clevis 802b at a second axle 804b and the proximal clevis 802b is coupled to a distal end 806 of the shaft 602.

The wrist 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "pitch" articulation of the end effector 604, and movement about the second pivot axis $P_2$ provides "yaw" articulation of the end effector 604.

A plurality of drive cables 808 extend longitudinally within the shaft 602 and pass through the wrist 106 to be operatively coupled to the end effector 604. The drive cables 808 form part of the cable driven motion system briefly described above, and may be referred to and otherwise characterized as cables, bands, lines, cords, wires, ropes, strings, twisted strings, elongate members, etc. The drive cables 808 can be made from a variety of materials including, but not limited to, metal (e.g., tungsten, stainless steel, etc.) or a polymer.

The drive cables 808 extend proximally from the end effector 604 to the drive housing 608 (FIG. 6) where they are operatively coupled to various actuation mechanisms or devices housed (contained) therein to facilitate longitudinal movement (translation) of the drive cables 808. Selective actuation of the drive cables 808 causes the end effector 604 to articulate (pivot) relative to the shaft 602. Moving a given drive cable 808 constitutes applying tension (i.e., pull force) to the given drive cable 808 in a proximal direction, which causes the given drive cable 808 to translate and thereby cause the end effector 604 to move (articulate) relative to the shaft 602.

One or more actuation cables 810, shown as first actuation cables 810a and second actuation cables 810b, may also extend longitudinally within the shaft 602 and pass through the wrist 106 to be operatively coupled to the end effector 604. The actuation cables 810a,b may be similar to the drive cables 808 and also form part of the cable driven motion system. Selectively actuating the actuation cables 810*a,b* causes the end effector 604 to actuate, such as collapsing the first and second jaw members 610, 612 to crimp a surgical clip (not shown).

More specifically, the actuation cables 810*a,b* may be operatively coupled to a cam 812 that is slidably engageable with the jaw members 610, 612. One or more pulleys 814 may be used to receive and redirect the first actuation cables 810*a* for engagement with the cam 812. Longitudinal movement of the first actuation cables 810*a* correspondingly moves the cam 812 distally relative to the jaw members 610, 612. The distal end of the cam 812 includes a tapering recess or camming channel 816 formed therein for slidably receiving corresponding cam tracks 818 provided by the jaw members 610, 612. As the cam 812 is advanced distally, the camming channel 816 pushes (collapses) the jaw members 610, 612 toward one another, thereby crimping a surgical clip (not shown) disposed therebetween. Actuation of the second actuation cables 810*b* (one shown) pulls the cam 812 proximally, thereby allowing the jaw members 610, 612 to open again to receive another surgical clip.

Although not expressly depicted in FIG. 8, an assembly including, for example, a feedbar, a feeder shoe, and a clip track may be included at or near the end effector 604 to facilitate feeding surgical clips into the jaw members 610, 612. In some embodiments, the feedbar (or a connecting member) may be flexible and extend through the wrist 606.

Figure 9:
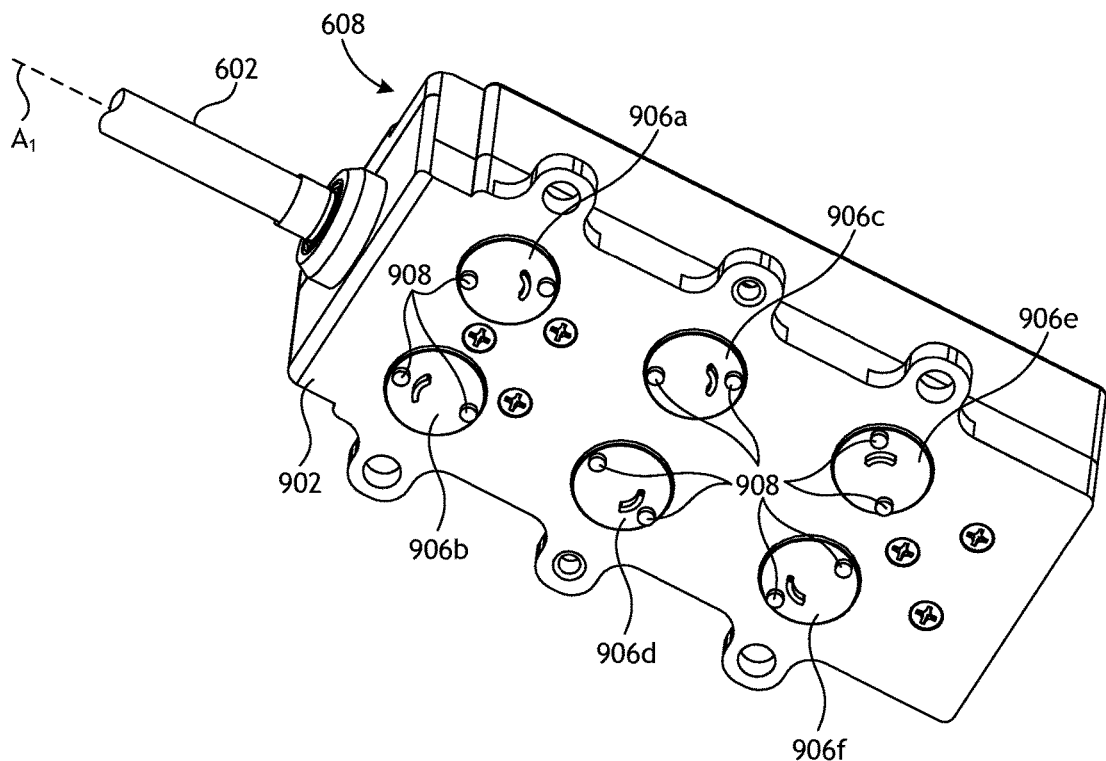
FIG. 9 is a bottom view of the drive housing of the surgical tool of FIG. 6.

FIG. 9 is a bottom view of the drive housing 608, according to one or more embodiments. As illustrated, the drive housing 608 may include a tool mounting interface 902 used to operatively couple the drive housing 608 to a tool driver of a robotic manipulator. The tool mounting interface 902 may mechanically, magnetically, and/or electrically couple the drive housing 608 to a tool driver.

As illustrated, the interface 902 includes and supports a plurality of drive inputs, shown as drive inputs 906*a*, 906*b*, 906*c*, 906*d*, 906*e*, and 906*f*. Each drive input 906*a-f* may comprise a rotatable disc configured to align with and couple to a corresponding input actuator (not shown) of a tool driver. Moreover, each drive input 906*a-f* provides or defines one or more surface features 908 configured to align with mating features provided on the corresponding input actuator. The surface features 908 can include, for example, various protrusions and/or indentations that facilitate a mating engagement.

In some embodiments, actuation of the first drive input 906*a* may control rotation of the elongate shaft 602 about its longitudinal axis $A_1$. Depending on the rotational actuation of the first drive input 906*a*, the elongate shaft 602 may be rotated clockwise or counter-clockwise. In some embodiments, selective actuation of the second and third drive inputs 906*b,c* may cause movement (axial translation) of the actuation cables 810*a,b* (FIG. 8), which causes the cam 812 (FIG. 8) to move and crimp a surgical clip, as generally described above. In some embodiments, actuation of the fourth drive input 906*d* feeds a surgical clip into the jaw members 610, 612 (FIG. 8). In some embodiments, actuation of the fifth and sixth drive inputs 906*e,f* causes movement (axial translation) of the drive cables 808 (FIG. 8), which results in articulation of the end effector 604. Each of the drive inputs 906*a-f* may be actuated based on user inputs communicated to a tool driver coupled to the interface 902, and the user inputs may be received via a computer system incorporated into the robotic surgical system.

Figure 10:
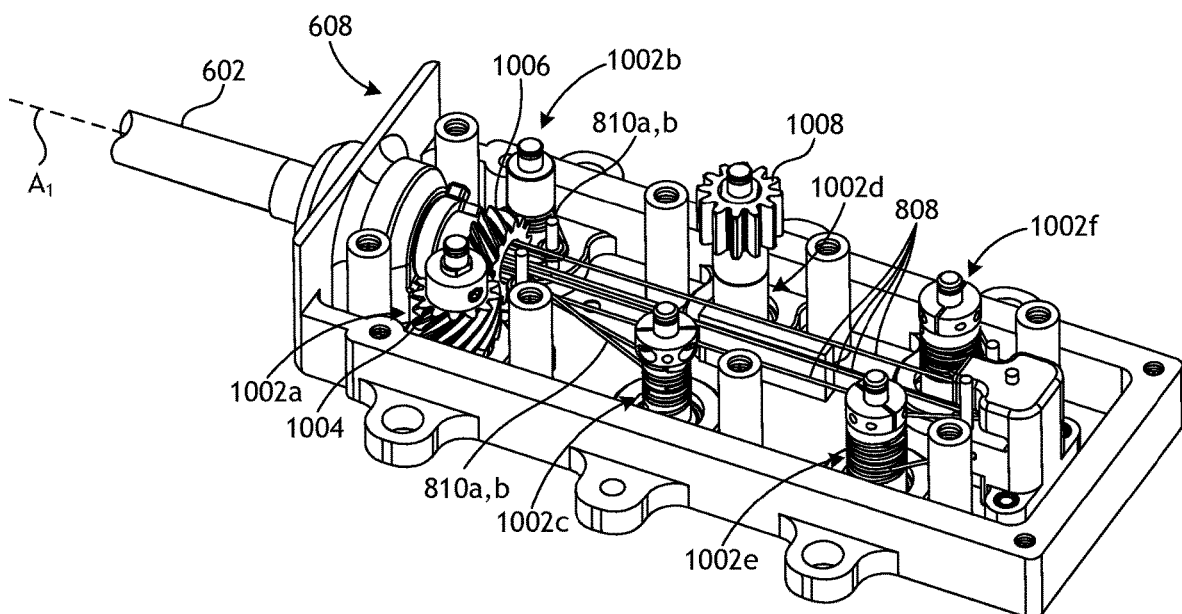
FIG. 10 is an isometric exposed view of the interior of the drive housing of the surgical tool of FIG. 6.

FIG. 10 is an isometric exposed view of the interior of the drive housing 608, according to one or more embodiments. Several component parts that may otherwise be contained within the drive housing 608 are not shown in FIG. 10 to enable discussion of the depicted component parts.

As illustrated, the drive housing 608 contains a first capstan 1002*a*, which is operatively coupled to or extends from the first drive input 906*a* (FIG. 9) such that actuation of the first drive input 906*a* results in rotation of the first capstan 1002*a*. A helical drive gear 1004 is coupled to or forms part of the first capstan 1002*a* and is configured to mesh and interact with a driven gear 1006 operatively coupled to the shaft 602 such that rotation of the driven gear 1006 correspondingly rotates the shaft 602. Accordingly, rotation of the helical drive gear 1004 (via actuation of the first drive input 906*a* of FIG. 9) will drive the driven gear 1006 and thereby control rotation of the elongate shaft 602 about the longitudinal axis $A_1$.

The drive housing 608 also includes second and third capstans 1002*b* and 1002*c* operatively coupled to or extending from the second and third drive inputs 906*b,c* (FIG. 9), respectively, such that actuation of the second and third drive inputs 906*b,c* results in rotation of the second and third capstans 1002*b,c*. The second and third capstans 1002*b,c* comprise capstan pulleys operatively coupled to the actuation cables 810*a,b* (FIG. 8) such that rotation of a given capstan 1002*b,c* actuates (longitudinally moves) a corresponding one of the actuation cables 810*a,b*. Accordingly, selective rotation of the second and third capstans 1002*b,c* via actuation of the second and third drive inputs 906*b,c*, respectively, will cause movement (axial translation) of the actuation cables 810*a,b*, which causes the cam 812 (FIG. 8) to move and crimp a surgical clip.

The drive housing 608 further includes a fourth capstan 1002*d*, which is operatively coupled to or extends from the fourth drive input 906*d* (FIG. 9) such that actuation of the fourth drive input 906*d* results in rotation of the fourth capstan 1002*d*. A spur gear 1008 is coupled to or forms part of the fourth capstan 1002*d* and is configured to mesh and interact with a rack gear (not shown) also contained within the drive housing 608. The rack gear may be operatively coupled to a feedbar (or another connecting member) which facilitates operation of a feeder shoe and associated clip track to feed surgical clips into the jaw members 610, 612 (FIGS. 6 and 8). Accordingly, rotation of the spur gear 1008 (via actuation of the fourth drive input 906*d*) will control the feedbar and thereby control loading of surgical clips into the jaw members 610, 612 as desired.

The drive housing 608 further contains or houses fifth and sixth capstans 1002*e* and 1002*f* operatively coupled to or extending from the fifth and sixth drive inputs 906*e,f* (FIG. 9), respectively, such that actuation of the fifth and sixth drive inputs 906*e,f* results in rotation of the fifth and sixth capstans 1002*e,f*.

The fifth and sixth capstans 1002*e,f* comprise capstan pulleys operatively coupled to the drive cables 808 (FIG. 8) such that rotation of a given capstan 1002*e,f* actuates (longitudinally moves) a corresponding one of the actuation cables 808. Accordingly, selective rotation of the fifth and sixth capstans 1002*e,f* via actuation of the fifth and sixth drive inputs 906*e,f*, respectively, will cause movement (axial translation) of the drive cables 808 and thereby articulate (pivot) the end effector 604 relative to the shaft 602.

The surgical tools 200, 600 described herein above may incorporate and facilitate the principles of the present disclosure in improving feeding and/or forming of surgical clips in robotic clip appliers. Moreover, it is contemplated herein to combine some or all of the features of the surgical tools 200, 600 to facilitate operation of the embodiments described herein. Accordingly, example surgical tools that may incorporate the principles of the present disclosure may include geared actuators, capstan pulley and cable actuators, or any combination thereof, without departing from the scope of the disclosure.

Figure 11:
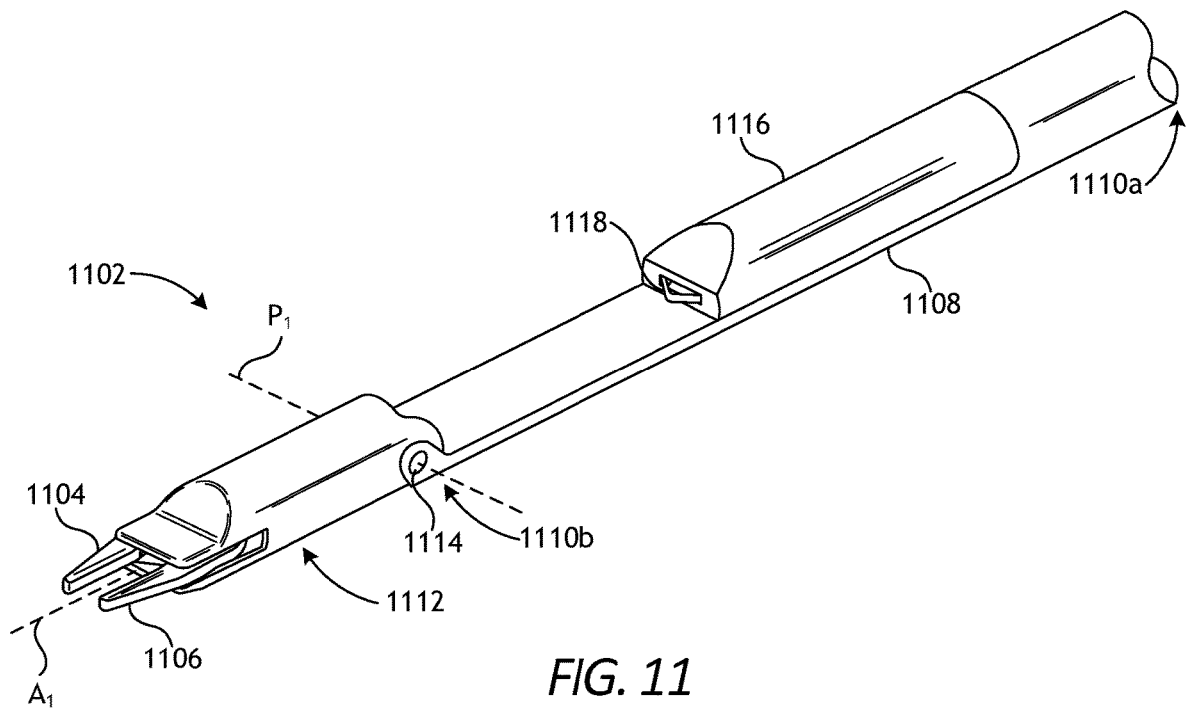
FIG. 11 is an enlarged isometric view of an example end effector.

FIG. 11 is an enlarged isometric view of an example end effector 1102, according to one or more embodiments the present disclosure. The end effector 1102 may be similar in some respects to the end effectors 204 and 604 of FIGS. 2 and 6, respectively. Similar to the end effectors 204, 604, for example, the end effector 1102 may be incorporated into either or both of the surgical tools 200, 600 described herein above. Moreover, the end effector 1102 may comprise a clip applier having opposed jaw members 1104 and 1106 configured to collapse toward one another to crimp a surgical clip. As described herein, the end effector 1102 may incorporate various component parts and actuatable mechanisms or features that facilitate the feeding of a surgical clip into the jaw members 1104, 1106 and collapsing the jaw members 1104, 1106 to crimp the surgical clip when desired.

As illustrated, the end effector 1102 includes an elongate body 1108 having a proximal end 1110a and a distal end 1110b. In some embodiments, the proximal end 1110a may be operatively coupled to an elongate shaft of a surgical tool, such as the shaft 202 of the surgical tool 200 of FIG. 2. In other embodiments, however, the proximal end 1110a may be operatively coupled to an articulable wrist joint, such as the wrist 606 of the surgical tool 600 of FIG. 6.

The end effector 1102 includes a head 1112 positioned or otherwise included at the distal end 1110b of body 1108. The head 1112 may be rotatably coupled to the body 1108 at a hinge or axle 1114, and the jaw members 1104, 1106 may be incorporated into or otherwise form part of the head 1112 such that rotation of the head 1112 on the axle 1114 correspondingly moves the jaw members 1104, 1106 in the same angular direction.

A pivot axis $P_1$ extends through the axle 1114 and is substantially perpendicular to a longitudinal axis $A_1$ of the effector 1102. The head 1112 may be pivotable about the pivot axis $P_1$ between a loading position, where the jaw members 1104, 1106 are positioned to receive a surgical clip, and a clamping position, where the jaw members 1104, 1106 are positioned and otherwise poised to clamp (crimp) a surgical clip at a desired location. As will be appreciated, the clamping position may be any angular position away from the loading position and relative to the longitudinal axis $A_1$ of the effector 1102 where the jaw members 1104, 1106 are able to properly crimp a surgical clip at a desired location. Accordingly, it is contemplated herein to deploy (crimp) a surgical clip at any angular location as long as it does not interfere with clip loading at the loading position. As will be appreciated, one advantage of the angular versatility of the head 1112 is that a user may be able to position the jaw members 1104, 1106 in a reverse position (i.e., retroflexion and/or retroflex articulation) relative to target tissue, which increases the maneuverability.

In some embodiments, the range of potential angular movement of the head 1112 may be about 180°. In such embodiments, the clamping position may comprise any angle between the loading position and 180° from the loading position. In practice, however, and to account for the loading position, the clamping position may comprise any angle between 0° and about 160° relative to the longitudinal axis $A_1$. In other embodiments, however, the range of potential angular movement of the head 1112 may be 360°. In such embodiments, the head 1112 may be capable of pivoting through the loading position in either angular direction and the clamping position may comprise virtually any angle relative to the longitudinal axis $A_1$. In embodiments where the head 1112 does not pivot through the loading position in either angular direction, and to account for the loading position, the clamping position may comprise any angle between 0° and about 160° in in either angular direction relative to the longitudinal axis $A_1$.

The end effector 1102 further includes a clip cartridge 1116 coupled to the body 1108 proximal to the head 1112 and configured to house one or more surgical clips 1118 (one partially shown). In some embodiments, the clip cartridge 1116 may be removably coupled to the body 1108, such as through the use of one or more mechanical fasteners (e.g., screws), an interference fit, a snap fit, any combination thereof, or the like. In such embodiments, the clip cartridge 1116 may be removed from the body 1108 when the supply of surgical clips 1118 is exhausted. The clip cartridge 1116 may then either be replaced with a new cartridge containing additional surgical clips, or additional surgical clips 1118 may be added to the clip cartridge 1116, which may then be reattached to the body 1108 for further operation. In other embodiments, however, the clip cartridge 1116 may form an integral part of the body 1108. In such embodiments, when the supply of surgical clips 1118 is exhausted the end effector 1102 may be replaced with a new end effector having a fresh supply of surgical clips.

Figure 12A:
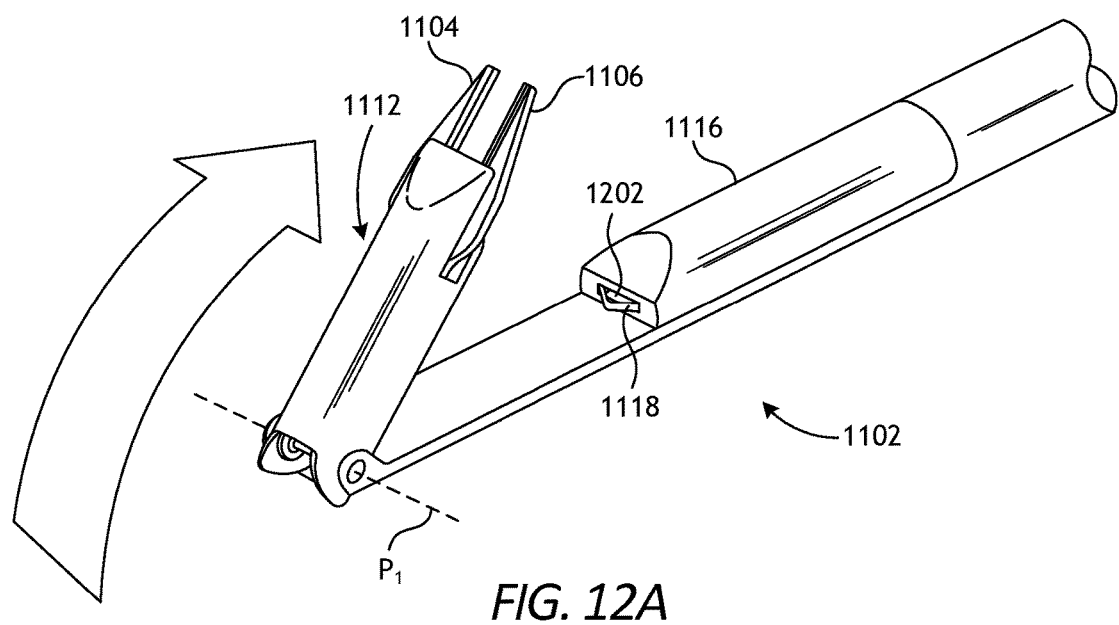
FIGS. 12A-12D are progressive isometric views of the end effector of FIG. 11 during example loading operation.

FIGS. 12A-12D depict progressive isometric views of the end effector 1102 during an example clip loading operation, according to one or more embodiments of the disclosure. In FIG. 12A, the head 1112 is shown in the process of being moved or rotated (pivoted) about the pivot axis $P_1$ toward the loading position where the jaw members 1104, 1106 become aligned or substantially aligned with a distal-most surgical clip 1118 to be received by the jaw members 1104, 1106. The distal-most surgical clip 1118 may be one of a plurality of surgical clips 1118 contained within the clip cartridge 1116, or may alternatively be the only or last surgical clip 1118 contained within the clip cartridge 1116. The means for actuating the head 1112 between the clamping and loading positions will be discussed in further detail below.

The clip cartridge 1116 may define an opening 1202 through which the surgical clips 1118 are discharged to be received by the jaw members 1104, 1106. In some embodiments, as illustrated, the crown of the distal-most surgical clip 1118 may protrude a short distance through the opening 1202 prior to being discharged from the clip cartridge 1116. In such embodiments, the opening 1202 may be slightly smaller than the dimensions of the surgical clip 1118 to prevent the surgical clip 1118 from prematurely or inadvertently advancing out of the clip cartridge 1116. In other embodiments, however, the distal-most surgical clip 1118 may be contained wholly within the clip cartridge 1116 prior to being discharged from the clip cartridge 1116 via the opening 1202.

Figure 12B:
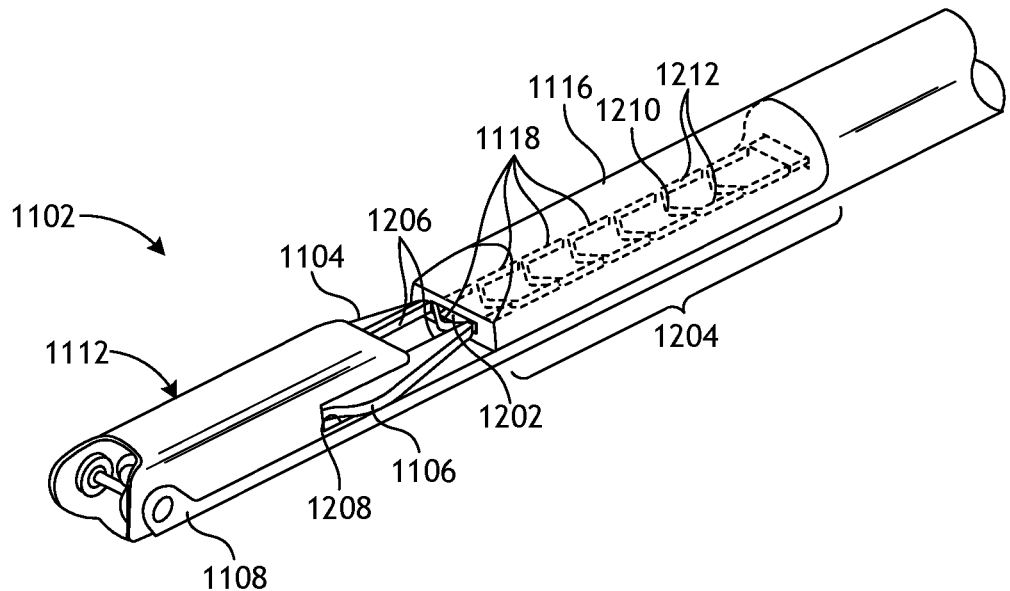

In FIG. 12B, the head 1112 is shown as having moved (pivoted) to the loading position where the jaw members 1104, 1106 are generally aligned with the distal-most surgical clip 1118. In some embodiments, each jaw member 1104, 1106 can include a channel or groove 1206 (better seen in FIG. 13A) formed on opposed inner surfaces thereof for receiving the distal-most surgical clip 1118. In such embodiments, the grooves 1206 may prove advantageous in helping to capture and maintain the surgical clip 1118 in a known position between the jaw members 1104, 1106. In other embodiments, however, the grooves 1206 may be omitted and the distal-most surgical clip 1118 may instead be captured or held by the jaw members 1104, 1106 via an interference fit or the like.

In some embodiments, the end effector 1102 may include a hard stop 1208 configured to receive and stop pivoting motion of the head 1112 at the loading position. In at least one embodiment, the body 1108 of the end effector 1102 may provide or define the hard stop 1208, but the hard stop 1208 may alternatively be a structure coupled to the body 1108. The hard stop 1208 may prove advantageous in helping maintain consistent loading alignment for the surgical clips 1118. In other embodiments, however, the hard stop 1208 may be omitted and the actuation mechanisms that facilitate pivoting movement of the head 1112 may be configured to precisely align the jaw members 1104, 1106 with the distal-most surgical clip 1118.

The clip cartridge 1116 is depicted in FIG. 12B in phantom and thereby exposing a set 1204 of surgical clips 1118 that might be contained within the clip cartridge 1116. While seven surgical clips 1118 are shown in the set 1204, it will be appreciated that more or less than seven may be contained within the clip cartridge 1116, without departing from the scope of the disclosure. Indeed, in at least one embodiment, the set 1204 may comprise a single surgical clip 1118.

Each surgical clip 1118 includes a crown 1210 (alternately referred to as an "apex") and a pair of legs 1212 extending longitudinally from the crown 1210. As illustrated, the surgical clips 1118 are positioned end-to-end within the clip cartridge 1116 with the legs 1212 of the more distal surgical clips 1118 resting on the crown 1210 of the more proximal surgical clips 1118. Accordingly, the surgical clips 1118 are arranged within the clip cartridge 1116 with the crown 1210 leading and the legs 1212 extending proximally therefrom. As a result, the surgical clips 1118 are fed crown 1210 first into the jaw members 1104, 1106. In contrast, conventional robotic clip appliers typically feed surgical clips legs first into opposed jaw members. Surgical clips are commonly designed to exhibit a slight taper, where the angle of the legs 1212 extending from the crown 1210 converge. This helps facilitate wedging the clips into the jaws legs first. One disadvantage of this clip design is that it reduces the clip-to-jaw retention capability since the legs are more tapered than the jaw. This also reduces allowable tip width between the jaw members, which correspondingly limits the size of tissue that can be treated.

Feeding the surgical clips 1118 crown first 1210 into the jaw members 1104, 1106 advantageously helps mitigate the surgical clips 1118 from getting caught on any sharp corners or the like that might obstruct their distal advancement. In embodiments including the grooves 1206 (FIGS. 12B and 13A) defined on each jaw member 1104, 1106, the legs 1212 may spring outward and seat themselves within the grooves 1206 after having exited the clip cartridge 1116 by bypassing the smaller-sized opening 1202. Moreover, feeding the surgical clips 1118 crown first 1210 into the jaw members 1104, 1106 allows a clip design where the legs 1212 can diverge, which increases clip to jaw retention and maximizes the allowable tip width between the jaw members 1104, 1106, and thereby increasing the size of tissue that can be treated.

Figure 12C:
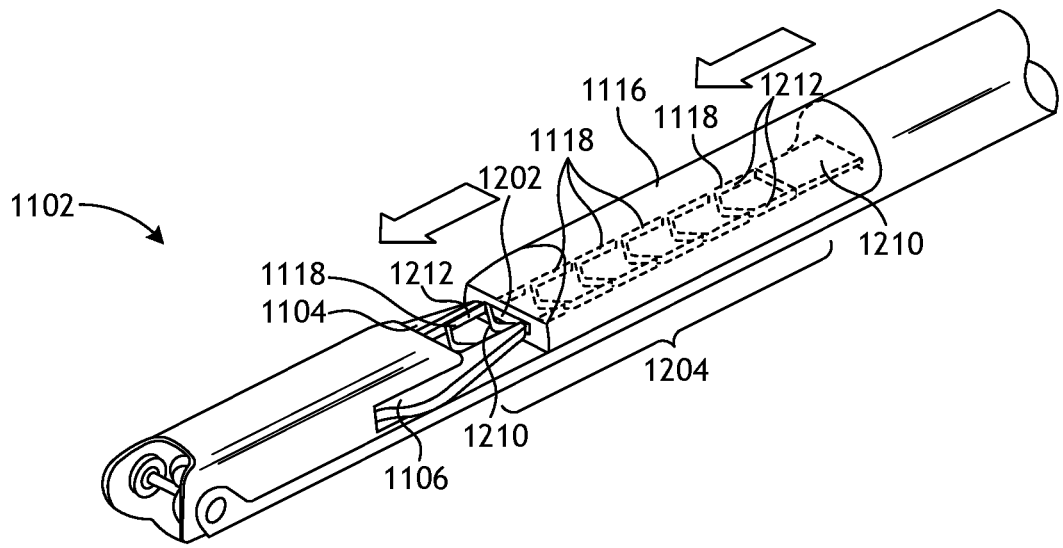

In FIG. 12C, the distal-most surgical clip 1118 has been advanced distally out of the clip cartridge 1116 and received by the jaw members 1104, 1106. As the distal-most surgical clip 1118 is received by the jaw members 1104, 1106, the penultimate surgical clip 1118 may correspondingly advance distally until its crown 1210 protrudes a short distance out of the opening 1202. In other embodiments, however, the penultimate surgical clip 1118 may remain entirely contained within the clip cartridge 1116 when the distal-most surgical clip 1118 has been received by the jaw members 1104, 1106, without departing from the scope of the disclosure.

Advancing the set 1204 of surgical clips 1118 distally to discharge the distal-most surgical clip 1118 from the clip cartridge 1116 may be accomplished by actuating (moving) a clip pusher 1210. The clip pusher 1210 may comprise any type of structure capable of applying an axial load on the set 1204 and thereby moving the set 1204 distally. For example, the clip pusher 1210 may comprise any rigid or semi-rigid rod, shaft, or planar structure (e.g., an elongate strip-like structure), or any combination thereof. In the illustrated embodiment, the clip pusher 1210 comprises a type of planar pusher bar, but could alternatively comprise another rigid or semi-rigid structure. The clip pusher 1210 is depicted herein as merely one example, and those skilled in the art will readily appreciate that many different configurations of the clip pusher 1210 may be employed, without departing from the scope of the disclosure.

In the illustrated embodiment, the clip pusher 1210 is depicted as being in contact with the legs 1212 of the proximal-most surgical clip 1118. Because of the end-to-end arrangement of the surgical clips 1118, pushing the proximal-most surgical clip 1118 will correspondingly move the remaining surgical clips 1118 in the set 1204 in the same direction. In other embodiments, however, the clip pusher 1210 may be configured to engage any other portion of the proximal-most surgical clip 1118. In yet other embodiments, the clip pusher 1210 may be configured to engage a combination of two or more surgical clips 1118 to apply the required axial load on the set 1204 to move the set 1204 distally, without departing from the scope of the disclosure.

The clip pusher 1210 may apply an axial load on the surgical clips 1118 sufficient to advance the set 1204 distally and discharge the distal-most surgical clip 1118 from the clip cartridge 1116 via the opening 1202. In some embodiments, actuation and distal movement of the clip pusher 1210 may be precisely controlled to deliver the exact amount of force and linear travel necessary to push (force) the distal-most surgical clip 1118 through the smaller-sized opening 1202 and feed the distal-most surgical clip 1118 into the jaw members 1104, 1106.

In some embodiments, the clip pusher 1210 may extend proximally to a drive housing (e.g., the drive housings 206, 606 of FIGS. 2 and 6, respectively), which may include a drive input and corresponding actuating mechanisms configured to actuate (move) the clip pusher 1210 as needed. In other embodiments, the clip pusher 1210 may be operatively coupled to or otherwise form part of a clip feeding assembly including, for example, a flexible or rigid feedbar (e.g., the feedbar 418 of FIG. 4) that extends from the drive housing and is actuated to correspondingly move the clip pusher 1210 distally and proximally as desired.

Figure 12D:
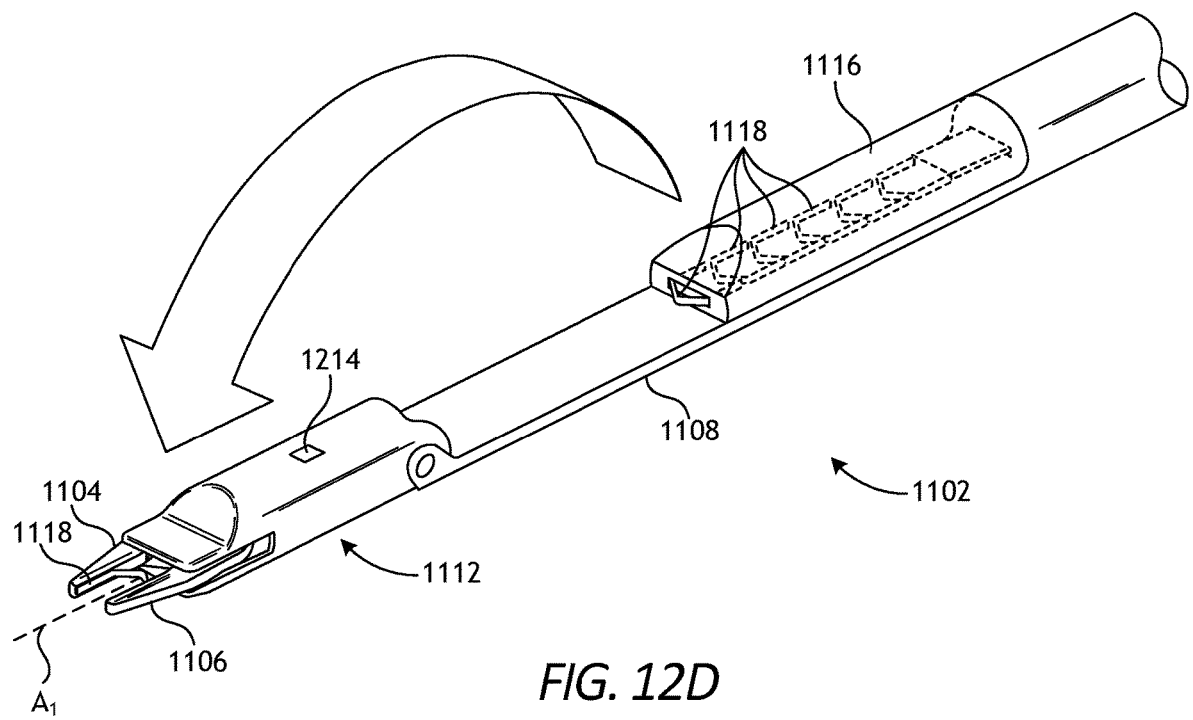

In FIG. 12D, the head 1112 is shown as having moved (pivoted) away from the loading position to a clamping position. As mentioned above, the clamping position for the head 1112 may be any angular position away from the loading position and relative to or aligned with the longitudinal axis $A_1$. In the illustrated embodiment, for example, the head 1112 is depicted as being aligned or substantially aligned with the longitudinal axis $A_1$, but could alternatively be angularly offset from the longitudinal axis $A_1$.

The surgical clip 1118 received within the jaw members 1104, 1106 is now ready to be deployed to ligate desired body tissue, for example, a blood vessel, a duct, a shunt, etc. Once the jaw members 1104, 1106 are properly positioned around or at the desired body tissue, the end effector 1102 may be actuated to collapse the jaw members 1104, 1106 and thereby crimp the surgical clip 1118 onto the body tissue.

The foregoing process of shown and described with respect to FIGS. 12A-12D can be repeated until the remaining surgical clips 1118 are depleted from the clip cartridge 1116, at which point the clip cartridge 1116 may be removed to add additional surgical clips 1118. The restocked clip cartridge 1116 may then be reattached to the body 1108 for further operation. Otherwise, the end effector 1102 as a whole may be replaced with a clip cartridge stocked with additional clips.

Still referring to FIG. 12D, in some embodiments, the end effector 1102 may further include one or more proximity sensors 1214 (one shown) configured to sense and/or detect adjacent body structures or tissue during operation. In the illustrated embodiment, the proximity sensor 1214 is depicted as being coupled to or positioned on the head 1112, but might alternatively be positioned at other locations on the end effector 1102. The sensor 1214 may prove advantageous in helping determine when the head 1112 may safely pivot between the clamping and loading positions without coming into contact or otherwise damaging sensitive body structures or tissue.

The sensor 1214 may be communicably coupled (wired or wirelessly) to a robotic controller (e.g., controllers 102a,b of FIG. 1) operated by a user, and the user may be updated in real-time as to the position of the head 1112 relative to sensitive body tissue. The real-time updates will help the user safely pivot the head 1112 without contacting anything vital or obstructing its movement.

Figure 13A:
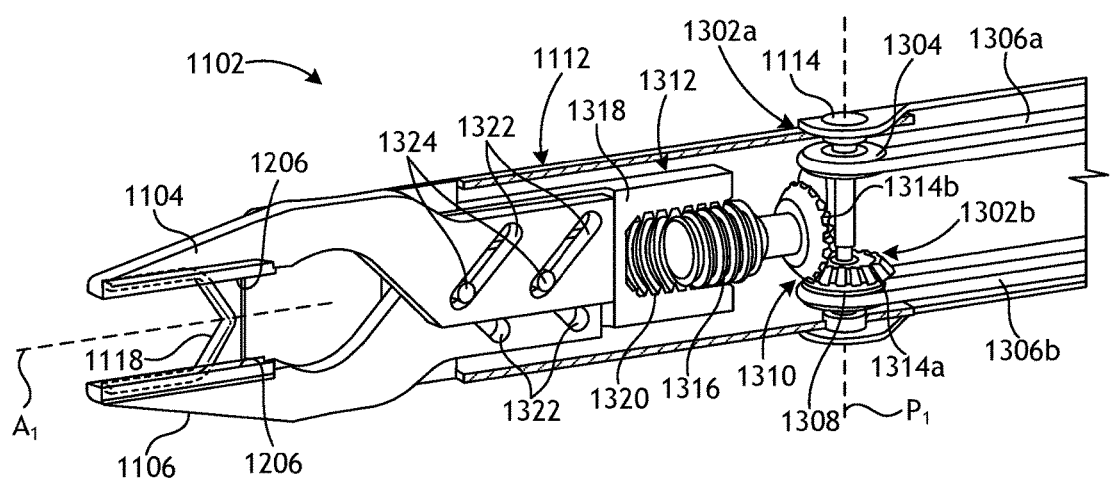
FIGS. 13A-13B are exposed, partial cross-sectional side views of the end effector of FIG. 11 during example operation.
Figure 13B:
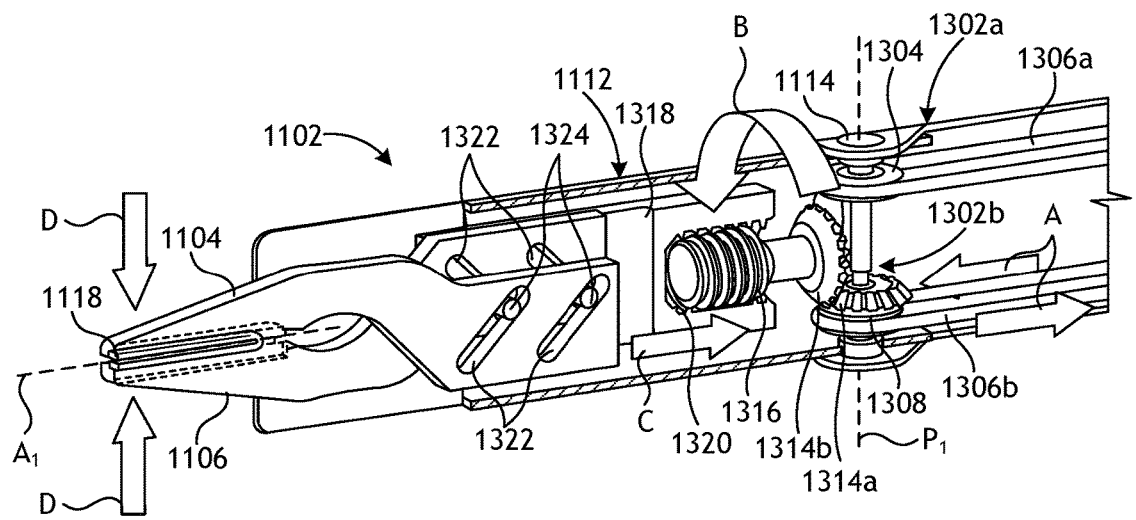

FIGS. 13A and 13B are exposed, partial cross-sectional side views of the end effector 1102, according to one or more embodiments. More specifically, FIG. 13A depicts the end effector 1102 prior to crimping a surgical clip 1118 between the jaw members 1104, 1106, and FIG. 13B shows the end effector 1102 following actuation to collapse the jaw members 1104, 1106. The end effector 1102 includes a rotational actuator 1302a operable to move (pivot) the head 1112 between the loading and clamping positions, and further includes a linear actuator 1302b operable to actuate the jaw members 1104, 1106 to crimp the surgical clip 1118.

The rotational actuator 1302a may comprise any device or mechanism capable of or configured to pivot the head 1112 between the loading position and any clamping position. In the illustrated embodiment, the rotational actuator 1302a includes an articulation pulley 1304 mounted to the axle 1114 such that rotation of the articulation pulley 1304 correspondingly rotates the axle 1114. A first drive cable 1306a may be routed around the articulation pulley 1304 to cause rotation of the articulation pulley 1304 when translated longitudinally. Since the head 1112 is operatively coupled to the axle 1114, rotation of the articulation pulley 1304, as acted upon by the first drive cable 1306a, simultaneously causes the head 1112 to rotate in the same angular direction.

The first drive cable 1306a may be similar to the drive cables 808 of FIG. 8. Moreover, the first drive cable 1306a may extend from a drive housing (e.g., the drive housings 206, 606 of FIGS. 2 and 6, respectively) and may be operatively coupled to a corresponding actuating mechanism or device positioned within the drive housing and configured to cause longitudinal translation of the first drive cable 1306a. In one embodiment, for example, the first drive cable 1306a may be operatively coupled to one or more capstan pulleys, such as any of the rotatable capstans 1002a-f of FIG. 10. In other embodiments, the first drive cable 1306a may be operatively coupled and otherwise extend from one or more translatable driven gears, such as the first and second driven gears 504a,b of FIG. 5. In yet other embodiments, the first drive cable 1306a may be operatively coupled to any combination of capstan pulley and driven gear, without departing from the scope of the disclosure.

The linear actuator 1302b may comprise any device or mechanism capable of or configured to move (collapse) the jaw members 1104, 1106 toward each other and thereby crimp the surgical clip 1118 disposed therebetween. In the illustrated embodiment, for example, the linear actuator 1302b includes a jaw pulley 1308, a bevel gear assembly 1310 operatively coupled to the jaw pulley 1308, and a threaded linear drive 1312 operatively coupled to the bevel gear assembly 1310. Rotation of the jaw pulley 1308 may cause actuation of the bevel gear assembly 1310, which, in turn, may cause actuation of the threaded linear drive 1312, which operates to collapse and open the jaw members 1104, 1106.

More specifically, the jaw pulley 1308 may be rotatably mounted to the axle 1114, but loosely mounted such that rotation of the jaw pulley 1308 does not rotate or otherwise act on the axle 1114. A second drive cable 1306b may be routed around the jaw pulley 1308 to cause rotation of the jaw pulley 1308. Similar to the first drive cable 1306a, the second drive cable 1306b may be similar to the drive cables 808 of FIG. 8 and may extend from a drive housing (e.g., the drive housings 206, 606 of FIGS. 2 and 6, respectively) where it is operatively coupled to a corresponding actuating mechanism or device configured to cause longitudinal translation of the second drive cable 1306b.

The bevel gear assembly 1310 may include a beveled drive gear 1314a coupled to or forming part of the jaw pulley 1308 and a corresponding beveled driven gear 1314b positioned to be driven (rotated) by the drive gear 1314a. Moreover, the threaded linear drive 1312 may include a worm gear 1316 operatively coupled to or extending from the driven gear 1314b, and a threaded gear plate 1318 that provides a female threading 1320 configured to threadably mate with or engage the helical threading defined on the worm gear 1316.

Example operation of the rotational actuator 1302a and the linear actuator 1302b is now provided. To move (pivot) the head 1112 between any clamping position and the loading position, and otherwise about the pivot axis $P_1$, the first drive cable 1306a may be translated (moved) in either longitudinal direction. Movement of the first drive cable 1306a rotates the articulation pulley 1304, which correspondingly rotates the axle 1114 about the pivot axis $P_1$. Since the head 1112 is operatively coupled to the axle 1114, rotation of the axle 1114 will simultaneously cause the head 1112 to rotate in the same angular direction. The longitudinal movement of the first drive cable 1306a may be precisely controlled to place the jaw members 1104, 1106 in the loading position and to otherwise accurately align the jaw members 1104, 1106 with a distal-most surgical clip for loading. Likewise, longitudinal movement of the first drive cable 1306a may be precisely controlled to position or otherwise orient the head 1112 in a desired clamping position away from the loading position.

When it is desired to crimp the surgical clip 1118 positioned between the jaw members 1104, 1106, the second drive cable 1306b may be translated (moved) in a first driving direction, as indicated by the arrows A (FIG. 13B). As the second drive cable 1306b translates, the jaw pulley 1308 and the drive gear 1314a are correspondingly rotated relative to the axle 1114, and the drive gear 1314a transmits a rotational load to the driven gear 1314*b*, which correspondingly rotates in a first angular direction, as indicated by the arrow B (FIG. 13B). As the driven gear 1314*b* rotates, the helical threading on the worm gear 1316 interacts with the female threading 1320 on the gear plate 1318 and thereby urges (drives) the gear plate 1318 in a first linear direction, as indicated by the arrow C (FIG. 13B).

As illustrated, the jaw members 1104, 1106 comprise independent or separate plate-like structures that are configured to move laterally relative to one another to collapse and crimp the surgical clip 1118. Each jaw member 1104, 1106 may provide and otherwise define one or more angled slots 1322 that extend at an angle offset from the longitudinal axis $A_1$ of the end effector 1102. While two angled slots 1322 are shown on each jaw member 1104, 1106, it will be appreciated that more or less than two may be employed, without departing from the scope of the disclosure. The angled slots 1322 of each jaw member 1104, 1106 may extend at equal but opposite angles. More particularly, the slots 1322 of the first jaw member 1104 may extend at a positive angle relative to the longitudinal axis $A_1$, while the slots 1322 of the second jaw member 1106 may extend at a negative angle of the same magnitude relative to the longitudinal axis $A_1$. As a result, depending on the axial direction, the angled slots 1322 diverge from or converge toward each other along the longitudinal axis $A_1$ of the end effector 1102.

As illustrated, one or more transition pins 1324 extend from the gear plate 1318 and extend through the angled slots 1322 of each jaw member 1104, 1106 when the jaw members 1104, 1106 are installed in the end effector 1102. The jaw members 1104, 1106 may be positioned within the head 1112 such that they are prevented from moving axially relative to the head 1112, but able to move laterally and thus collapse towards one another or open. As the rotating worm gear 1316 rotates, the gear plate 1318 correspondingly moves in the first linear direction C (FIG. 13B), which simultaneously moves the transition pins 1324 in the same direction. The transition pins 1324 slidingly engage the angled slots 1322 and, because of the oppositely angled configuration of the angled slots 1322, the transition pins 1324 will urge the jaw members 1104, 1106 to transition (move) laterally with respect to each other, as indicated by the oppositely directed arrows D (FIG. 13B). As the jaw members 1104, 1106 collapse toward each other in the direction D, the surgical clip 1118 will be crimped or crushed therebetween.

The jaw members 1104, 1106 may be re-opened to receive another un-crimped surgical clip by reversing the foregoing procedure. More specifically, the second drive cable 1306*b* may be translated (moved) in a second driving direction opposite the first driving direction A, which will rotate the jaw pulley 1308 and the drive gear 1314*a* in the opposite direction relative to the axle 1114, and the driven gear 1314*b* will correspondingly rotate in a second angular direction opposite the first angular direction B. Rotating the driven gear 1314*b* in the second angular direction will unthread the worm gear 1316 from the gear plate 1318, which urges (drives) the gear plate 1318 in a second linear direction opposite the first linear direction C. As the gear plate 1318 moves in the second linear direction, the transition pins 1324 also move in the same direction within and slidingly engage the angled slots 1322, which urges the jaw members 1104, 1106 to separate from each other in a direction opposite the direction D.

In some embodiments, as the head 1112 is rotated via actuation of the rotational actuator 1302*a*, the bevel gear assembly 1310 may be affected and may inadvertently reverse rotate as driven gear 1314*b* walks along the drive gear 1314*a* in the direction of rotation of the head 1112. To prevent the worm gear 1316 from unintentionally advancing caused by the bevel gear assembly 1310 reverse rotating during movement of the head 1112, the bevel gear assembly 1310 may be actuated to compensate for the reverse rotation. More specifically, the second drive cable 1306*b* may be actuated to back rotate the jaw pulley 1308 and the coupled drive gear 1314*a* to cancel out inadvertent movement of the bevel gear assembly 1310 during movement of the head 1112. As will be appreciated, such back rotation of the jaw pulley 1308 may be automated, such as through a software-driven application.

The independent or separate plate-like structures of the jaw members 1104, 1106 may prove advantageous in effecting parallel closure of the jaw members 1104, 1106, which dramatically reduces the force required to crimp a surgical clip. As used herein, the phrase "parallel closure" refers to the relative parallel disposition of the opposing inner surfaces of the jaw members 1104, 1106 throughout their entire range of motion as the jaw members 1104, 1106 move between open and closed positions. Parallel closure is often used with respect to medical device end effectors and is desirable to minimize tissue damage due to non-uniform pressure or milking (squeezing out) of tissue from between opposed jaw members.

Conventional clip appliers typically include a cam that moves distally to slidingly engage opposed and connected jaw members. As the cam advances over the jaw members, the jaw members act as individual cantilever beams as they are urged toward one another by the cam. Because the jaw members act as cantilever beams, the distal ends or "tips" of the jaw members come together first, at which point each jaw member is effectively converted into a fixed-pinned beam, which increases the stiffness of the system. As opposed fixed-pinned beams, the lateral force required to fully close the jaw members along the length of the grooves defined on each jaw member increases dramatically. Consequently, this requires more expensive and powerful actuators to move (actuate) the cam and necessitates more robust materials used to make the jaws, the cam, and other intervening structural elements that facilitate jaw actuation.

According to embodiments of the present disclosure, the independent or separate plate-like jaw members 1104, 1106 eliminate distal tip-to-tip closure. Rather, the jaw members 1104, 1106 may be designed to achieve parallel (or substantially parallel) closure. As used herein, the term "substantially parallel" can refer to true relative parallelism between opposing members or near true relative parallelism, without departing from the scope of the disclosure. Eliminating tip-to-tip closure eliminates the need to deflect the jaw members 1104, 1106 between supported ends, which may prove advantageous in eliminating the additional reaction load from the opposing jaw member and minimizing jaw length.

Parallel closure dramatically reduces the force required to collapse the jaw members 1104, 1106 and helps facilitate uniform crimping of the surgical clip 1118. This advantageously allows smaller actuators to be used to collapse the jaw members 1104, 1106. Moreover, this allows the jaw members 1104, 1106 to be made of less-expensive materials and manufactured through less-expensive manufacturing processes. In some embodiments, for example, the jaw members 1104, 1106 may be made of an injection molded plastic. In other embodiments, the jaw members 1104, 1106 may be made of a metal and molded through a metal injection molding process. In yet other embodiments, the jaw members 1104, 1106 may be made of a plastic or a metal and manufactured via an additive manufacturing process (e.g., 3D printing). In even further embodiments, the jaw members 1104, 1106 may be made of a metallic base with plastic overmolding, without departing from the scope of the disclosure.

Figure 14:
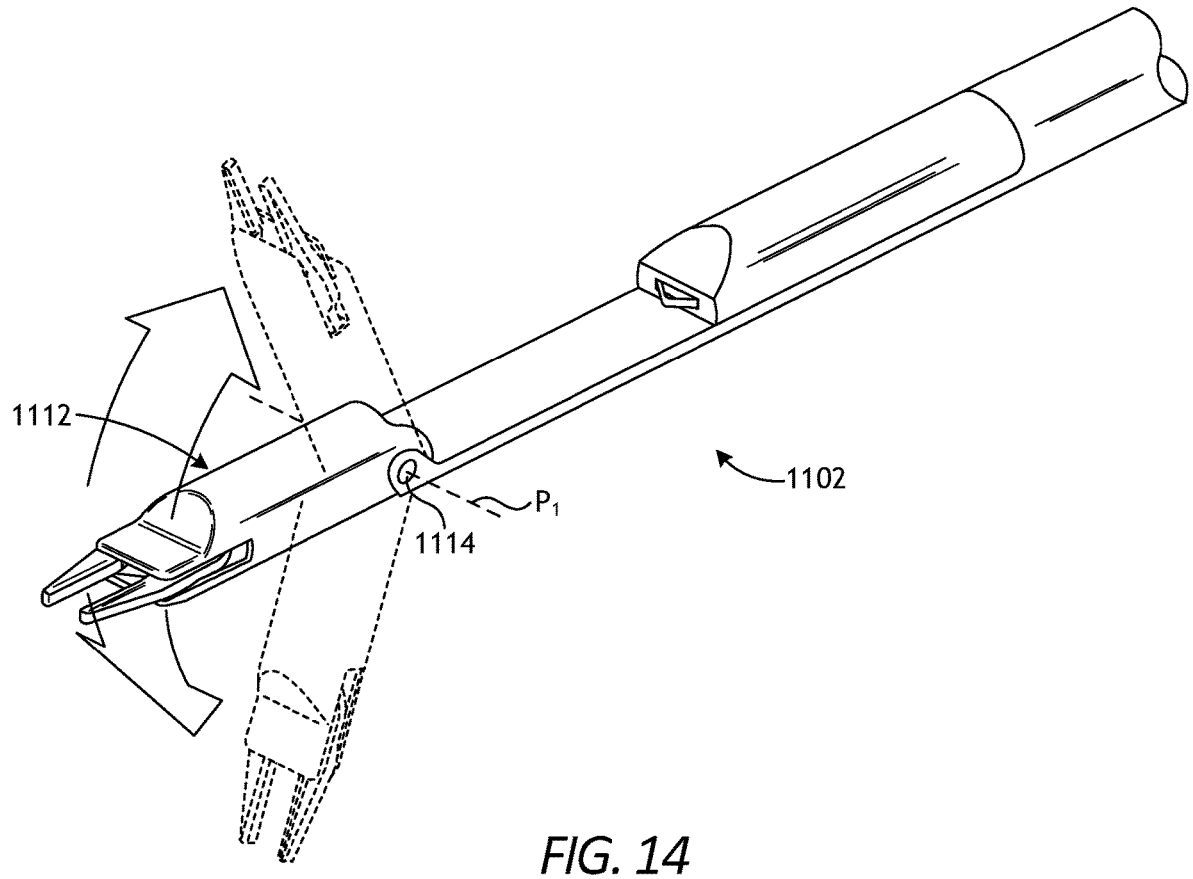
FIG. 14 is an isometric view of another example embodiment of the end effector of FIG. 11.

FIG. 14 is an isometric view of another example embodiment of the end effector 1102. In some embodiments, as briefly mentioned above, the range of potential angular movement of the head 1112 about the pivot axis P1 of the axle 1114 may be about 180°. In the illustrated embodiment, however, the range of potential angular movement of the head 1112 is depicted as being potentially 360° in either angular direction. This may prove advantageous in allowing the jaw members 1104, 1106 to be articulated to a wide range of angular clamping positions for clamping and deploying a surgical clip.

Embodiments disclosed herein include:

A. An end effector for a surgical clip applier that includes a body having a proximal end and a distal end, a clip cartridge coupled to the body and containing one or more surgical clips, a head rotatably coupled to the distal end, and first and second jaw members mounted to the head such that rotation of the head correspondingly moves the first and second jaw members, wherein the head is rotatable between a loading position, where the first and second jaw members are aligned to receive a distal-most surgical clip of the one or more surgical clips, and a clamping position, where the first and second jaw members are positioned to crimp a surgical clip interposing the first and second jaw members.

B. A method of operating an end effector of a surgical clip applier, the end effector including a body, a clip cartridge coupled to the body and containing one or more surgical clips, a head rotatably coupled to a distal end of the body, and first and second jaw members mounted to the head such that rotation of the head correspondingly moves the first and second jaw members, the method includes rotating the head to a loading position where the first and second jaw members are aligned to receive a distal-most surgical clip of the one or more surgical clips, advancing the distal-most surgical clip out of the clip cartridge and receiving the distal-most surgical clip between the first and second jaw members, rotating the head to a clamping position, and collapsing the first and second jaw members to crimp the distal-most surgical clip.

C. A surgical clip applier that includes a drive housing, an elongate shaft that extends from the drive housing, and an end effector arranged at a distal end of the elongate shaft, the end effector including a body having a proximal end and a distal end, a clip cartridge coupled to the body and containing one or more surgical clips, a head rotatably coupled to the distal end, and first and second jaw members mounted to the head such that rotation of the head correspondingly moves the first and second jaw members, wherein the head is rotatable between a loading position, where the first and second jaw members are aligned to receive a distal-most surgical clip of the one or more surgical clips, and a clamping position, where the first and second jaw members are positioned to crimp a surgical clip interposing the first and second jaw members.

Each of embodiments A, B, and C may have one or more of the following additional elements in any combination: Element 1: wherein the head can rotate about 180° relative to a longitudinal axis of the end effector. Element 2: wherein the head can rotate about 360° relative to a longitudinal axis of the end effector. Element 3: further comprising a groove defined in an inner surface of each of the first and second jaw members, wherein the groove of each jaw member is aligned with the distal-most surgical clip when the head is in the loading position. Element 4: wherein each surgical clip comprises a crown and a pair of legs extending from the crown, and wherein the distal-most surgical clip is fed crown first into the first and second jaw members from the clip cartridge. Element 5: further comprising a clip pusher configured to apply an axial load on the one or more surgical clips to position the distal-most surgical clip between the first and second jaw members. Element 6: further comprising a proximity sensor configured to sense adjacent body structures or tissue during operation. Element 7: wherein the clip cartridge is removably coupled to the body. Element 8: further comprising a rotational actuator operable to pivot the head between the loading and clamping positions, and a linear actuator operable to collapse and open the first and second jaw members. Element 9: wherein the rotational actuator comprises an articulation pulley mounted to the axle such that rotation of the articulation pulley correspondingly rotates the axle, and a drive cable routed around the articulation pulley to cause rotation of the articulation pulley, wherein the head is operatively coupled to the axle such that rotation of the articulation pulley causes the head to rotate. Element 10: wherein the linear actuator comprises a jaw pulley rotatably mounted to the axle, a drive cable routed around the jaw pulley to cause rotation of the jaw pulley, a bevel gear assembly operatively coupled to the jaw pulley, and a threaded linear drive operatively coupled to the bevel gear assembly, wherein rotation of the jaw pulley causes actuation of the bevel gear assembly, which, in turn, causes actuation of the threaded linear drive, which operates to collapse and open the first and second jaw members. Element 11: wherein the first and second jaw members comprise independent structures movable laterally relative to one another to achieve parallel closure. Element 12: further comprising a first angled slot defined in the first jaw member and extending at a positive angle relative to a longitudinal axis of the end effector, a second angled slot defined in the second jaw member and extending at a negative angle relative to the longitudinal axis, wherein the negative angle is of a same magnitude as the positive angle, and a transition pin that extends from a gear plate of the linear actuator and through the first and second angled slots, wherein actuation of the linear actuator moves the gear plate in a linear direction and correspondingly moves the transition pin to slidingly engage the first and second angled slots and thereby urge the first and second jaw members laterally with respect to each other, and wherein opposing inner surfaces defined on the first and second jaw members remain substantially parallel to each other as the first and second jaw members move laterally with respect to each other.

Element 13: wherein each surgical clip comprises a crown and a pair of legs extending from the crown, and wherein receiving the distal-most surgical clip between the first and second jaw members comprises feeding the distal-most surgical clip crown first into the first and second jaw members from the clip cartridge. Element 14: wherein the head is rotatably coupled to an axle at the distal end and the method further comprises rotating the head between the loading and clamping positions with a rotational actuator, the rotational actuator comprising an articulation pulley mounted to the axle such that rotation of the articulation pulley correspondingly rotates the axle, and a drive cable routed around the articulation pulley to cause rotation of the articulation pulley, wherein the head is operatively coupled to the axle such that rotation of the articulation pulley causes the head to rotate. Element 15: further comprising collapsing and opening the first and second jaw members with a linear actuator, the linear actuator comprising a jaw pulley rotatably mounted to the axle, a drive cable routed around the jaw pulley to cause rotation of the jaw pulley, a bevel gear assembly operatively coupled to the jaw pulley, and a threaded linear drive operatively coupled to the bevel gear assembly, wherein rotation of the jaw pulley causes actuation of the bevel gear assembly, which, in turn, causes actuation of the threaded linear drive, which operates to collapse and open the first and second jaw members. Element 16: wherein the first and second jaw members comprise independent structures and collapsing the first and second jaw members further comprises moving the first and second jaw members laterally relative to one another to achieve parallel closure.

Element 17: further comprising an articulable wrist joint interposing the end effector and the elongate shaft.

By way of non-limiting example, exemplary combinations applicable to A, B, and C include: Element 8 with Element 9; Element 8 with Element 10; Element 8 with Element 11; Element 11 with Element 12; and Element 15 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector for a surgical clip applier, comprising:
a body having a proximal end and a distal end;
a clip cartridge coupled to the body and containing one or more surgical clips, each surgical clip having a crown and a pair of legs extending from the crown;
a head rotatably coupled to the distal end; and
first and second jaw members mounted to the head such that rotation of the head correspondingly moves the first and second jaw members,
wherein the head is rotatable between a loading position, where the first and second jaw members are aligned to receive a distal-most surgical clip of the one or more surgical clips, and a clamping position, where the first and second jaw members are positioned to crimp a surgical clip interposing the first and second jaw members, and
wherein the distal-most surgical clip is fed crown first into the first and second jaw members from the clip cartridge.

2. The end effector of claim 1, wherein the head can rotate about 180° relative to a longitudinal axis of the end effector.

3. The end effector of claim 1, wherein the head can rotate about 360° relative to a longitudinal axis of the end effector.

4. The end effector of claim 1, further comprising a groove defined in an inner surface of each of the first and second jaw members, wherein the groove of each jaw member is aligned with the distal-most surgical clip when the head is in the loading position.

5. The end effector of claim 1, further comprising a clip pusher configured to apply an axial load on the one or more surgical clips to position the distal-most surgical clip between the first and second jaw members.

6. The end effector of claim 1, further comprising a proximity sensor configured to sense adjacent body structures or tissue during operation.

7. The end effector of claim 1, wherein the clip cartridge is removably coupled to the body.

8. The end effector of claim 1, further comprising:
a rotational actuator operable to pivot the head between the loading and clamping positions; and
a linear actuator operable to collapse and open the first and second jaw members.

9. The end effector of claim 8, wherein the rotational actuator comprises:
an articulation pulley mounted to the axle such that rotation of the articulation pulley correspondingly rotates the axle; and
a drive cable routed around the articulation pulley to cause rotation of the articulation pulley, wherein the head is operatively coupled to the axle such that rotation of the articulation pulley causes the head to rotate.

10. The end effector of claim 8, wherein the linear actuator comprises:
a jaw pulley rotatably mounted to the axle;
a drive cable routed around the jaw pulley to cause rotation of the jaw pulley;
a bevel gear assembly operatively coupled to the jaw pulley; and
a threaded linear drive operatively coupled to the bevel gear assembly, wherein rotation of the jaw pulley causes actuation of the bevel gear assembly, which, in turn, causes actuation of the threaded linear drive, which operates to collapse and open the first and second jaw members.

11. The end effector of claim 8, wherein the first and second jaw members comprise independent structures movable laterally relative to one another to achieve parallel closure.

12. The end effector of claim 11, further comprising:
a first angled slot defined in the first jaw member and extending at a positive angle relative to a longitudinal axis of the end effector;
a second angled slot defined in the second jaw member and extending at a negative angle relative to the longitudinal axis, wherein the negative angle is of a same magnitude as the positive angle; and
a transition pin that extends from a gear plate of the linear actuator and through the first and second angled slots,
wherein actuation of the linear actuator moves the gear plate in a linear direction and correspondingly moves the transition pin to slidingly engage the first and second angled slots and thereby urge the first and second jaw members laterally with respect to each other,
and wherein opposing inner surfaces defined on the first and second jaw members remain substantially parallel to each other as the first and second jaw members move laterally with respect to each other.

13. A method of operating an end effector of a surgical clip applier, comprising:
positioning the end effector adjacent a patient for operation, the end effector including:
a body having a proximal end and a distal end;
a clip cartridge coupled to the body and containing one or more surgical clips, each surgical clip having a crown and a pair of legs extending from the crown;
a head rotatably coupled to the distal end; and
first and second jaw members mounted to the head such that rotation of the head correspondingly moves the first and second jaw members;
rotating the head to a loading position where the first and second jaw members are aligned to receive a distal-most surgical clip of the one or more surgical clips;
advancing the distal-most surgical clip out of the clip cartridge and receiving the distal-most surgical clip crown first between the first and second jaw members;
rotating the head to a clamping position; and
collapsing the first and second jaw members to crimp the distal-most surgical clip.

14. The method of claim 13, wherein the head is rotatably coupled to an axle at the distal end and the method further comprises:
rotating the head between the loading and clamping positions with a rotational actuator, the rotational actuator comprising:
an articulation pulley mounted to the axle such that rotation of the articulation pulley correspondingly rotates the axle; and
a drive cable routed around the articulation pulley to cause rotation of the articulation pulley, wherein the head is operatively coupled to the axle such that rotation of the articulation pulley causes the head to rotate.

15. The method of claim 13, further comprising collapsing and opening the first and second jaw members with a linear actuator, the linear actuator comprising:
a jaw pulley rotatably mounted to the axle;
a drive cable routed around the jaw pulley to cause rotation of the jaw pulley;
a bevel gear assembly operatively coupled to the jaw pulley; and
a threaded linear drive operatively coupled to the bevel gear assembly,
wherein rotation of the jaw pulley causes actuation of the bevel gear assembly, which, in turn, causes actuation of the threaded linear drive, which operates to collapse and open the first and second jaw members.

16. The method of claim 15, wherein the first and second jaw members comprise independent structures and collapsing the first and second jaw members further comprises moving the first and second jaw members laterally relative to one another to achieve parallel closure.

17. A surgical clip applier, comprising:
a drive housing;
an elongate shaft that extends from the drive housing; and
an end effector arranged at a distal end of the elongate shaft, the end effector including:
a body having a proximal end and a distal end;
a clip cartridge coupled to the body and containing one or more surgical clips, each surgical clip having a crown and a pair of legs extending from the crown;
a head rotatably coupled to the distal end; and
first and second jaw members mounted to the head such that rotation of the head correspondingly moves the first and second jaw members,
wherein the head is rotatable between a loading position, where the first and second jaw members are aligned to receive a distal-most surgical clip of the one or more surgical clips, and a clamping position, where the first and second jaw members are positioned to crimp a surgical clip interposing the first and second jaw members, and
wherein the distal-most surgical clip is fed crown first into the first and second jaw members from the clip cartridge.

18. The surgical clip applier of claim 17, further comprising an articulable wrist joint interposing the end effector and the elongate shaft.

* * * * *